US012773536B2

(12) United States Patent
Folan

(10) Patent No.: US 12,773,536 B2
(45) Date of Patent: Oct. 27, 2026

(54) DRAINAGE DEVICES AND METHODS OF USE

(71) Applicant: Boston Scientific Scimed, Inc., Maple Grove, MN (US)

(72) Inventor: Martyn G. Folan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1252 days.

(21) Appl. No.: 17/556,456

(22) Filed: Dec. 20, 2021

(65) Prior Publication Data

US 2022/0203077 A1 Jun. 30, 2022

Related U.S. Application Data

(60) Provisional application No. 63/131,381, filed on Dec. 29, 2020.

(51) Int. Cl.

*A61M 27/00* (2006.01)
*A61F 2/00* (2006.01)
*A61F 2/90* (2013.01)
*A61F 2/966* (2013.01)

(52) U.S. Cl.

CPC ......... *A61M 27/002* (2013.01); *A61F 2/0077* (2013.01); *A61F 2/90* (2013.01); *A61F 2/9661* (2020.05); *A61F 2/9662* (2020.05); *A61F 2250/0097* (2013.01); *A61F 2250/0098* (2013.01)

(58) Field of Classification Search

CPC ........ A61F 2/90; A61F 2/9661; A61F 2/0077; A61F 2220/0008; A61M 27/002; A61B 17/11

See application file for complete search history.

(56) References Cited

U.S. PATENT DOCUMENTS 6,007,544 A * 12/1999 Kim ............... A61B 17/320016 606/108
6,143,015 A * 11/2000 Nobles ............ A61B 17/12109 604/96.01
2004/0167572 A1* 8/2004 Roth ................ A61B 17/12181 606/219
2009/0198315 A1 8/2009 Boudjemline
2009/0210048 A1 8/2009 Amplatz et al.
2009/0312834 A1 12/2009 Wood et al.
2010/0241218 A1 9/2010 Bruszewski et al.
(Continued)

FOREIGN PATENT DOCUMENTS

JP 201770512 4/2017
JP 2017513652 A 6/2017
(Continued)

OTHER PUBLICATIONS

International Search Report and Written Opinion dated Apr. 8, 2022 for International Application No. PCT/US2021/064389.

*Primary Examiner* — Ariana Zimbouski

(74) *Attorney, Agent, or Firm* — Seager, Tufte & Wickhem, LLP

(57) ABSTRACT

The present disclosure is related to medical devices, stents, drainage devices, and the like, which feature a doubled back design. Various embodiments described herein have a portion with overlapping layers, at least one of which may comprise a cover.

16 Claims, 11 Drawing Sheets

(56) References Cited

U.S. PATENT DOCUMENTS

| | | | | |
|---|---|---|---|---|
| 2013/0012969 | A1* | 1/2013 | Shin | A61F 2/064 606/155 |
| 2013/0073026 | A1* | 3/2013 | Russo | A61B 17/12109 606/198 |
| 2016/0135941 | A1 | 5/2016 | Binmoeller et al. | |
| 2018/0361127 | A1* | 12/2018 | Gray | A61F 2/90 |
| 2019/0254804 | A1 | 8/2019 | Folan et al. | |

FOREIGN PATENT DOCUMENTS

| | | | |
|---|---|---|---|
| KR | 1020180071413 | | 6/2018 |
| WO | 2012103531 | A2 | 8/2012 |
| WO | 2015195893 | A1 | 12/2015 |

* cited by examiner

DRAINAGE DEVICES AND METHODS OF USE

PRIORITY

The present application is a non-provisional of, and claims the benefit of priority under 35 U.S.C. § 119 to, U.S. Provisional Application Ser. No. 63/131,381, filed Dec. 29, 2020, the disclosures of which are herein incorporated herein by reference in their entirety for all purposes.

FIELD

The present disclosure relates generally to the field of medical devices and establishing fluid communication between body lumens. In particular, the present disclosure relates to devices and methods for establishing a controlled flow or access passage between body lumens.

BACKGROUND

The desire to establish access between two body lumens to create fluid communication from one to the other is present under various circumstances and conditions. A variety of medical devices (e.g., anastomotic devices, drainage stents, etc.) are able to establish open flow or access passages between body lumens. For example, during a procedure, an anastomotic or drainage device may be implanted to facilitate drainage from the bile duct into the stomach or duodenum.

To establish and maintain appropriate drainage, migration of the anastomotic or drainage device may be minimized within or between body lumens. Furthermore, leakage of the drainage device may also be minimized. For example, leakage from a drainage device into the peritoneal cavity after an anastomotic procedure may result in pain or infection in a patient. Post-acute bleeding, for example, may contribute to pain and infection risk for patients through abrasions and the exposure thereof to potentially dangerous material, such as digestive fluids or necrotic tissue.

With the above considerations in mind, a variety of advantageous medical outcomes may be realized by the devices and/or methods of the present disclosure.

SUMMARY

In one aspect of the present disclosure, a medical device may comprise an elongate tubular body comprising first and second end portions. The elongate body may have a constrained configuration and an unconstrained configuration. A first end portion of the elongate tubular body may be doubled back towards the second end into a retention member. The elongate tubular body may comprise a coating or covering of the retention member. The coating may extend beyond the first end portion towards the second end portion along a partial axial length of the medical device.

In the above and other aspects, an uncovered segment of the first end portion may extend beyond the retention member towards the second end portion. The uncovered segment may extend beyond the retention member radially outward of the covering or coating. The second end portion may be uncovered. The retention member may be fully covered. The retention member may comprise at least one flange. The retention member may comprise a smooth end surface. The smooth end surface may comprise at least one of a flush, flat, curved, or curled surface. The coating or covering may extend towards the second end portion along at least 50% of a full axial length of the medical device. The coating or covering may extend towards the second end portion along at least 70% of a full axial length of the medical device. The elongate tubular body in the unconstrained configuration may be configured to facilitate fluid flow without leakage between the second end portion and the retention member. The medical device may comprise a full axial length of approximately 8-10 cm, wherein the retention member comprises a diameter of approximately 8-10 mm, or both. The medical device may comprise a second retention member in the unconstrained configuration. The second retention member may comprise a flare, step, bulb, raised braid segment, or any combination thereof. The medical device may comprise at least one radiopaque, echogenic, colored, or otherwise imageable marker. The medical device may be a self-expanding stent.

In another aspect, a medical device may comprise an elongate tubular body including first and second end portions. The first end portion may be doubled back towards the second end portion. The first end portion may be doubled back to form a retention member. The retention member may include a coating extending longitudinally beyond the first end portion towards the second end portion. The medical device may have a constrained configuration and an unconstrained configuration.

In the above and other aspects, an uncovered segment of the first end portion may extend beyond the retention member towards the second end portion. The uncovered segment may extend beyond the retention member radially outward of the covering or coating. The second end portion may be uncovered. The retention member may be fully covered. The retention member may comprise at least one flange. The retention member may comprise a smooth end surface. The smooth end surface may comprise at least one of a flush, flat, curved, or curled surface. The coating or covering may extend towards the second end portion along at least 50% of a full axial length of the medical device. The coating or covering may extend towards the second end portion along at least 70% of a full axial length of the medical device. The elongate tubular body in the unconstrained configuration may be configured to facilitate fluid flow without leakage between the second end portion and the retention member. The medical device may comprise a full axial length of approximately 8-10 cm, wherein the retention member comprises a diameter of approximately 8-10 mm, or both. The medical device may comprise a second retention member in the unconstrained configuration. The second retention member may comprise a flare, step, bulb, raised braid segment, or any combination thereof. The medical device may comprise at least one radiopaque, echogenic, colored, or otherwise imageable marker. The medical device may be a self-expanding stent.

In another aspect, a medical device may comprise an elongate body having a constrained configuration and an unconstrained configuration. In the unconstrained configuration, the elongate body may comprise a first end and a second end. The medical device may comprise a retention member at the first end, the retention member formed of a doubled back woven filament. The medical device may comprise a first portion extending from the retention member towards the second end. The first portion may have a covering extending towards the second end from the retention member at least partially along an axial length of the first portion. The medical device may comprise a second portion extending towards the second end from the retention member along a radially outer surface of the first portion.

The second portion may have a shorter axial length than the first portion. The second portion may be uncovered.

In the above and other aspects of the present disclosure, the retention member may comprise a covering. The retention member may comprise at least one flange. The covering may extend towards the second end along at least 50% of the axial length of the medical device. The medical device may comprise a second retention member in the unconstrained configuration. The second retention member may include a flare, step, bulb, raised braid segment, or any combination thereof. The medical device may comprise at least one radiopaque, echogenic, colored, or otherwise imageable marker.

In one embodiment of the present disclosure, a method may comprise advancing an uncovered first portion of a medical device through an opening in a first body lumen into a second body lumen. The method may comprise proximally retracting an outer sheath slidably disposed about the medical device to a first position in the first body lumen such that the first portion is unconstrained to partially extend into the second body lumen. The method may comprise proximally retracting the outer sheath to a second position in the first body lumen such that a second portion of the medical device moves to an unconstrained configuration. The unconstrained configuration of the second portion may comprise a retention member including a doubled back portion of the second portion. The retention member may be positioned in the first body lumen. The unconstrained configuration of the second portion may comprise a covering extending between the first body lumen and the second body lumen.

In another aspect of the present disclosure, a stent or other medical device may comprise an elongate tubular body having a constrained configuration and an unconstrained configuration. In the unconstrained configuration, a proximal portion of the elongate tubular body may be doubled back into a proximal retention member. The elongate tubular body may comprise a coating or covering which, in the unconstrained configuration, extends distally beyond the proximal portion along a distal portion of the elongate tubular body. The elongate tubular body may define a lumen extending therethrough.

In an aspect of the present disclosure, a stent or other medical device may comprise an elongate tubular body having a constrained configuration and an unconstrained configuration. A proximal portion of the elongate tubular body may be doubled back into a proximal retention member. The elongate body may comprise a coating or covering which, in the unconstrained configuration, covers the proximal retention member and extends distally beyond the proximal portion. The coating or covering may extend distally along a partial length of a distal portion of the elongate tubular body.

In another aspect of the present disclosure, a medical device may comprise an elongate body having a constrained configuration and an unconstrained configuration. In the constrained configuration, a coating or covering may extend along a partial axial length of the elongate body. In the unconstrained configuration, the elongate body may comprise an inner cylindrical body. The inner cylindrical body may comprise a cover or coating along at least a portion of an axial length of the elongate body in the unconstrained configuration. The elongate body in the unconstrained configuration may comprise a proximal portion doubled back into a proximal retention member. The proximal portion may be continuously formed with the inner cylindrical body. The elongate body in the unconstrained configuration may comprise an outer cylindrical body. The outer cylindrical body may extend distally from the proximal retention member along an outer covered surface of the inner cylindrical body. The outer cylindrical body may be uncovered. The outer cylindrical body may be continuously formed with the proximal portion. The outer cylindrical body may have a shorter axial length than the inner cylindrical body.

In an additional aspect of the present disclosure, a method may comprise advancing a medical device into a first body lumen. The medical device may include an elongate tubular body with a constrained configuration and an unconstrained configuration. In at least the unconstrained configuration, the elongate tubular body may comprise a proximal portion doubled back into a proximal retention member. A first portion may extend distally from the proximal retention member. The first portion may have a proximal covered segment and a distal uncovered segment. A second portion may extend distally from the proximal retention member along a radially outward surface of the first portion. The second portion may be uncovered. The second portion may have a shorter axial length than the proximal covered segment of the first portion. The method may include advancing the medical device through an opening in the first body lumen. The method may include advancing the medical device across a space between the first body lumen and a second body lumen. The method may include advancing the medical device into the second body lumen. The method may include unconstraining the distal uncovered segment in the second body lumen. The method may include unconstraining the proximal portion of the elongate tubular body in the first body lumen. The proximal retention member may be deployed in the first body lumen based on the unconstraining of the proximal portion. The space between the first body lumen and the second body lumen may be spanned by at least a portion of the proximal covered segment.

In yet another aspect of the present disclosure, a method may comprise advancing a portion of a medical device through an opening in a first body lumen into a second body lumen. The medical device may comprise a constrained configuration and an unconstrained configuration. The method may include proximally retracting an outer sheath slidably disposed about the medical device to a first position in the first body lumen. The first portion may be unconstrained based on the retraction of the outer sheath. The first portion may partially extend into the second body lumen based on the retraction of the outer sheath. The method may further include proximally retracting the outer sheath to a second position in the first body lumen such that a second portion of the medical device moves to the unconstrained configuration. The unconstrained configuration of the second portion may comprise a retention member. The retention member may be positioned in the first body lumen. The method may further include proximally retracting the outer sheath to unconstrain a third portion of the medical device such that the third portion doubles back to extend distally through a lumen of the first and second portions into the second body lumen.

In the above and other methods of the present disclosure, the medical device may comprise at least one radiopaque, echogenic, colored, or otherwise imageable marker. The method may comprise retracting the outer sheath to the first position, to the second position, or both, based on a position of the at least one radiopaque, echogenic, colored, or otherwise imageable marker. The medical device may comprise an uncovered portion extending distally from the retention member along at least a partial axial length of the covering. The uncovered portion may be configured to interact with a tissue wall of the first body lumen.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1A:
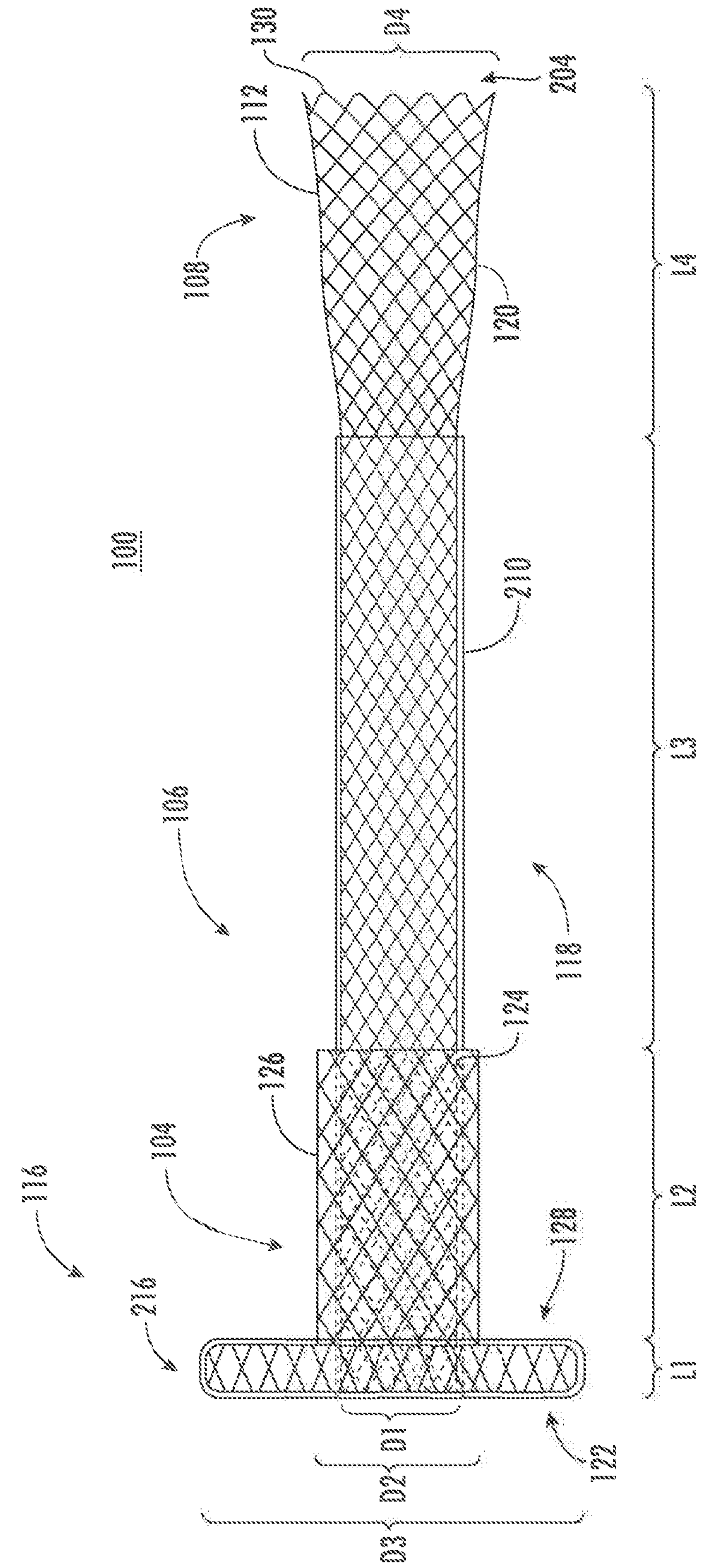
FIGS. 1A-1B illustrate side and perspective views of a medical device, according to at least one embodiment of the present disclosure.

The present disclosure is related to medical devices, stents, drainage devices, and the like, which feature a doubled back design, which may be similar to various devices described in the currently pending United States Provisional Patent Application titled "STENTS AND METHODS FOR USE AND MANUFACTURE OF STENTS WITH IMPROVED RETENTION MEMBERS," filed on Sep. 14, 2020 having U.S. Provisional Application No. 63/078,019 and incorporated by reference herein in its entirety for all purposes. Various embodiments described herein have a portion with overlapping layers, at least one of which may comprise a coating or cover. Doubled back medical device designs are contemplated which combine benefits of covered stent drainage capabilities and uncovered stent retentive strength to promote tissue in-growth.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices (e.g., anastomotic devices, stents, etc.) and methods for drainage of (or access to) the biliary system, it should be appreciated that such medical devices and methods may be used in a variety of medical procedures (e.g., external biliary drain conversion, enteroenterostomy, gastrojejumostomy, gastroduodenostomy and gastroileostomy, etc.) to establish and/or maintain a temporary or permanent open flow passage between or drainage from a variety of body organs, ducts, lumens, vessels, fistulas and spaces (e.g., the dermis, stomach, duodenum, gallbladder, bladder, kidneys, walled-off pancreatic necrosis (WOPN), abscesses, etc.). The devices can be inserted via different access points and approaches, (e.g., percutaneously, endoscopically, laparoscopically or some combination). Various stents described are self-expanding stents, but other embodiments where the stent is expandable by other means, for example, a balloon catheter, may be possible. Moreover, such medical devices are not limited to drainage, but may facilitate access to organs, vessels or body lumens for other purposes, such as creating a path to divert or bypass fluids or solids from one location to another, removing obstructions and/or delivering therapy, including non-invasive manipulation of the tissue within the organ and/or the introduction of pharmacological agents via the open flow passage. In some embodiments, devices, systems, and methods may comprise one or more similarities to the Drawings and/or Specification of United States Patent Application Publication No. 2019/0254804, titled "DRAINAGE DEVICE" and corresponding to currently pending U.S. application Ser. No. 16/279,140 filed on Feb. 19, 2019, which is presently incorporated by reference herein in its entirety for all purposes.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

It will be understood that various embodiments described herein may include one or more features discussed herein. For example, combinations of concepts relating to any aspects of the present disclosure are currently contemplated.

Figure 1B:
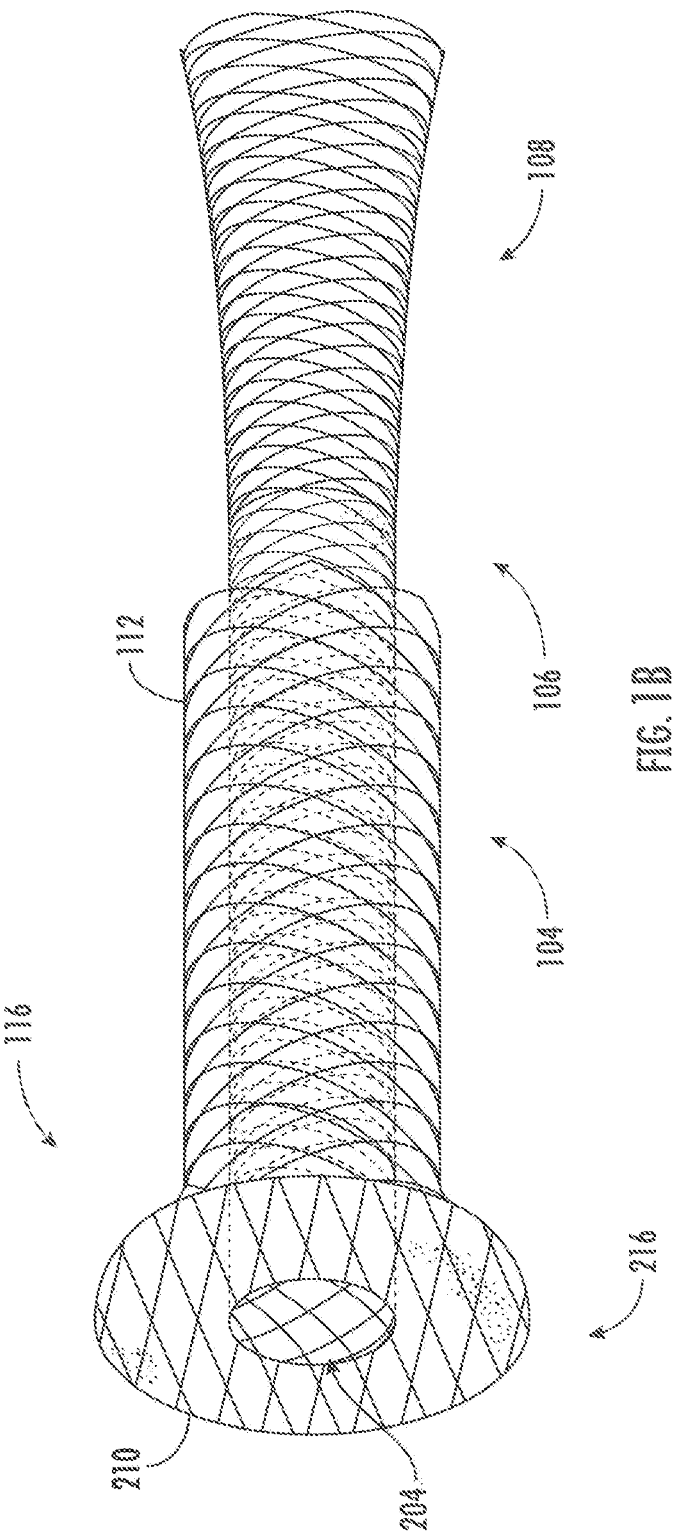

FIGS. 1A-1B illustrate side and perspective views of exemplary medical device 100 according to various embodiments described herein. Medical device 100 (e.g., stent, or drainage stent) may include an elongate tubular body 118 configured to move between a first (e.g., constrained, collapsed, non-expanded) configuration and a second (e.g., non-constrained, expanded) configuration. For the sake of brevity, a "first configuration" as referred to herein will be understood to collectively refer to a constrained configuration, collapsed configuration, non-expanded configuration, or the like. A "second configuration" as referred to herein will be understood to collectively refer to a constrained configuration, collapsed configuration, compressed configuration, non-expanded configuration, or the like. Embodiments are not limited in this context.

The elongate tubular body 118 may comprise a mesh, one or more braided wires, or woven filament 120, which may be formed of a polymer, metal, or other material. In many embodiments, the elongate tubular body 118 may be formed of a shape memory material, such as Nitinol or similar alloy.

For the sake of simplicity, the present disclosure may refer to a material of a stent as a woven filament or plurality of woven filaments, but embodiments may alternatively and/or additionally comprise other materials and/or configurations of filament.

The elongate tubular body 118 may comprise a coating or cover 210 extending at least partially along an axial length thereof. Cover 210 may comprise silicone, urethane, Chronoflex, polytetrafluoroethylene (pTFE), or other suitable material.

In the second configuration, the elongate tubular body 118 may comprise a first end portion 116 (e.g., a proximal or proximal end portion, region, or section), an opposite second end portion 108 (e.g., a distal or distal end portion, region, or section), and a central portion 106 (e.g., a saddle or central saddle portion, region, or section) extending therebetween. The first end portion 116 may comprise a retention member 216 and an overlap portion 104 which extends from the retention member 216 towards the second end portion 108. The overlap portion 104 may comprise a radially inner wall 124 and a radially outer wall 126. The elongate tubular body 118 may define a lumen 204 extending longitudinally therethrough.

Central portion 106 may be continuously formed with one or both of radially inner wall 124 and second end portion 108. Retention member 216 may be continuously formed with radially inner wall 124. Radially outer wall 126 may be continuously formed with retention member 216. In many embodiments, first end portion 116, central portion 106, and second end portion 108 can be formed from a single elongate frame or member, such as elongate body 200 of FIG. 2A, wherein retention member 216 and/or overlap portion 104 are formed by doubling back a portion of the single elongate frame or member over an adjacent portion of the single elongate frame or member so that an inner cylindrical body (e.g., radially inner wall 124, or radially inner wall 124 together with central portion 106) is disposed within and/or disposed to extend through a portion of an outer cylindrical body (e.g., radially outer wall 126). Accordingly, retention member 216 may be formed by a portion of a doubled-back woven filament.

The doubled-back configuration of overlap portion 104 may provide various benefits over conventional designs. For example, the layering of radially inner wall 124 and radially outer wall 126 may provide stability or mechanical rigidity to overlap portion 104. The doubled-back configuration of retention member 216 may increase a retentive force of the medical device 100 compared to corresponding retention members that do not include such a doubled-back configuration. For example, in order for the medical device 100 to migrate, retention member 216 as supported by radially inner wall 124 and radially outer wall 126 would have to deform, which may be less likely due to its doubled-back geometry. One or both of radially inner wall 124 and radially outer wall 126 can resist or oppose a deformation of retention member 216, thereby resulting in a greater pull-out force of retention member 216 as opposed to alternative designs.

In another benefit, the doubled-back configuration of overlap portion 104 may enable selective manufacturing of medical device 100 to enable placement of cover 210 in a desired location on the medical device 100. For example, in many embodiments, cover 210 may extend along a full length of central portion 106 and radially inner wall 124. Thus, lumen 204 may be separated from retention member 216 by a sufficient distance to prevent flow therethrough, thus preventing fluid from accumulating within the interior of retention member 216. Accordingly, risk of impaction and subsequent infection may be reduced as compared to conventional designs.

In some embodiments, cover 210 may extend over a portion of an elongate tubular body 118 corresponding to retention member 216 in the first configuration, such that the cover may cover all or part of a retention member in the second configuration. In some embodiments, cover 210 may extend beyond retention member 216 towards the second end portion 108 along a partial axial length of the medical device 100. For example, cover 210 is illustrated in FIGS. 1A-1B as extending fully around retention member 216 (along a full axial length "L1" of retention member 216, including second wall 128), but cover 210 may alternatively extend to cover only part of second wall 128, or to not cover second wall 128, to cover only first wall 122, or to cover only part of first wall 122. In some embodiments (not shown), cover 210 may extend beyond the retention member 216 along a partial axial or full axial length of radially outer wall 126. Accordingly, various embodiments may employ cover 210 to prevent fluid from leaking through or around retention member 216 through a lumen of a tissue wall spanned by medical device 100 (not shown). In many embodiments, however, at least a portion of radially outer wall 126 is uncovered.

Figure 5:
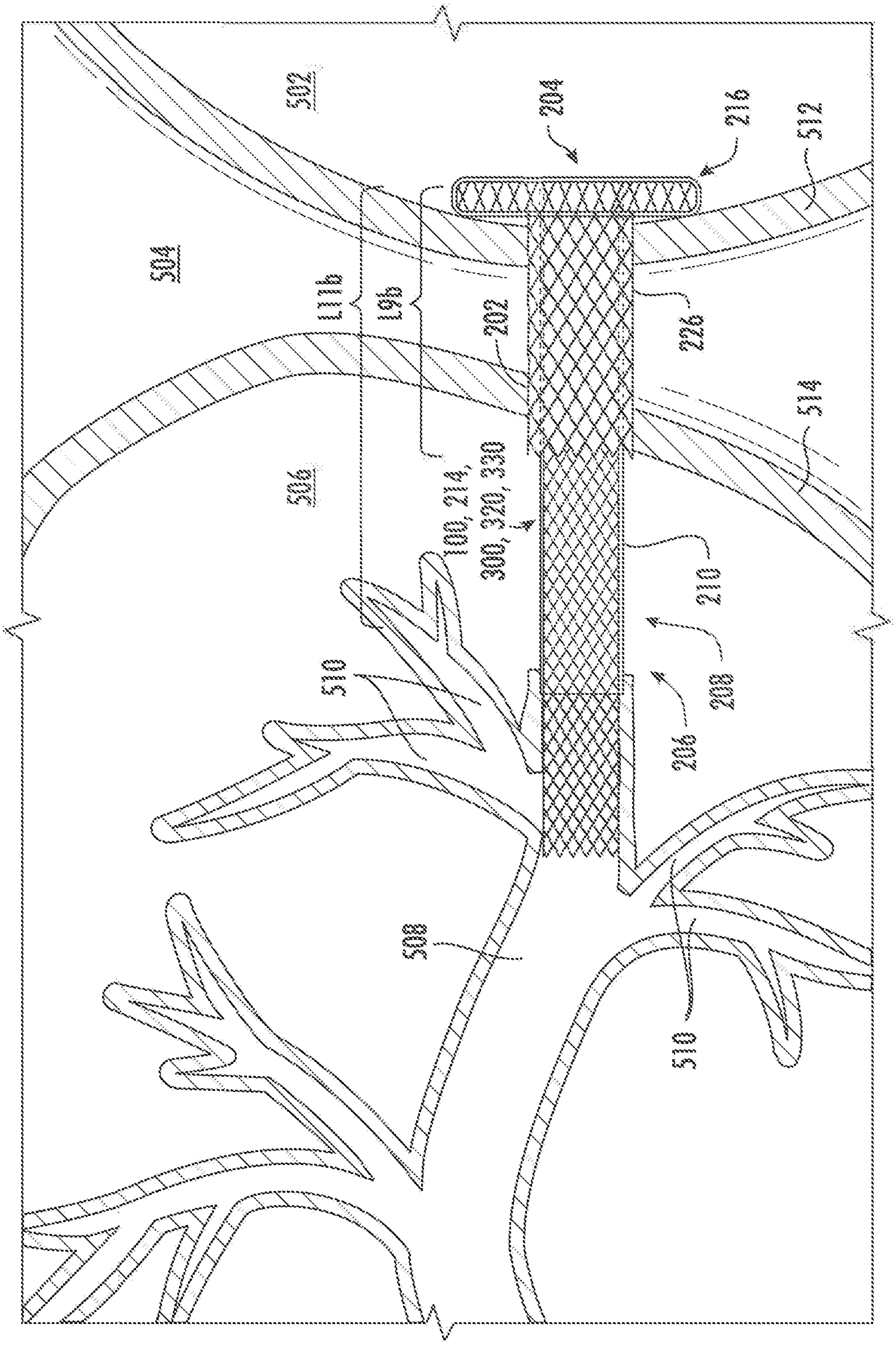
FIG. 5 illustrates a side view of a medical device deployed across first and second body lumens, according to at least one embodiment of the present disclosure.

Uncovered portions of medical device 100 may encourage tissue ingrowth, which can be desirable in order to prevent migration of medical device 100 after it has been appropriately positioned within the body. Thus, in addition to the resistance to migration presented by the mechanical support of retention member 216 by the overlap portion 104, the doubled-back configuration of present embodiments may allow for further resistance to migration based on the selective allowance of tissue ingrowth along first end portion 116. In many cases, overlap portion 104 may allow for ingrowth of one or more tissue walls, as illustrated in FIG. 5, into interstices of the woven filament 120 of medical device 100, into a space between radially inner wall 124 and radially outer wall 126, or both. It will be recognized that medical device 100 may present benefit(s) over conventional designs by providing both retentive benefits of uncovered stents (e.g., based on the interaction of tissue with overlap portion 104) and flow path integrity benefits of covered stents (e.g., based on the extent of cover 210 along an axial or longitudinal length of the medical device 100).

The retention member 216 may extend radially from (e.g., perpendicular to an outer surface of) the radially outer wall 126 and/or the radially inner wall 124 of the overlap portion 104. In many embodiments, the retention member 216 may comprise a flange, such as the double-walled flange illustrated. In other embodiments, retention member 216 can comprise a bulge, bulb, or other feature (not illustrated). Retention member 216 may comprise a first wall 122 and an opposite second wall 128, one or both of which may be configured to appose an associated tissue wall of a body lumen. It will be appreciated that the double-back design of retention member 216 may provide first wall 122 and/or second wall 128 with a smooth tissue-engaging surface. Providing such a smooth surface may desirably decrease the risk of abrasion of apposed tissues that are engaged by the first and/or second walls 122, 128. For the purposes of the present application, a smooth surface may be a flush, flat, curved, or curled end face, surface, or the like, particularly without one or more discontinuities such as welds or material terminations interrupting the surface that could abrade the apposed tissue(s) with which the surface interacts. First wall 122 and second wall 128 are illustrated with flat edges for the sake of simplicity, but it will be understood that one or both may comprise a curve, angle, or other surface variation (not illustrated), and that first wall 122 and second wall 128 may be parallel to one another or non-parallel.

As previously mentioned, second end portion 108 may, in many cases, be fully or partially uncovered. Accordingly, the uncovered portion may encourage tissue ingrowth to second end portion 108, limiting stent migration, and/or fluid flow may be allowed through the side of second end portion 108 into the lumen 204, either through pores or openings of the weave of woven filament 120 or through a dedicated window such as window 710 of FIG. 7, as discussed in greater detail below. Accordingly, the covered portion may be configured to facilitate fluid flow from one or more side ducts, such as are illustrated in FIG. 5, through second end portion 108.

Figure 2A:
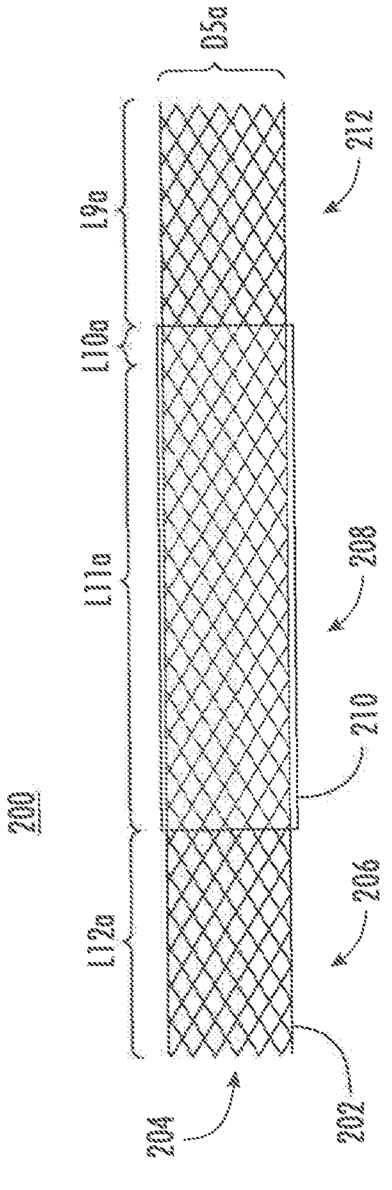
FIGS. 2A-2B illustrate side views of an unassembled and an assembled medical device, according to at least one embodiment of the present disclosure.
Figure 2B:
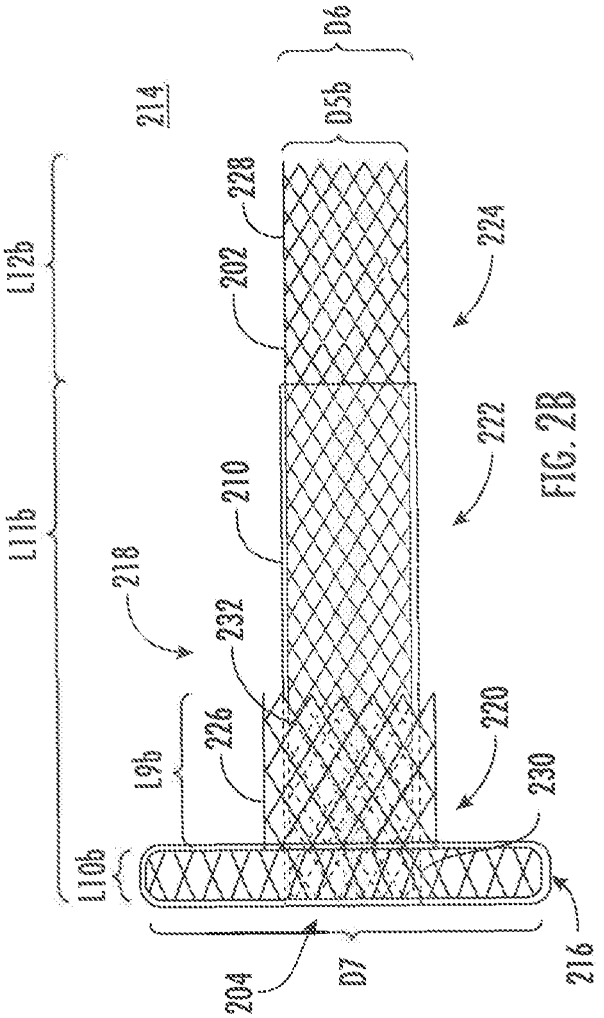
Figure 7:
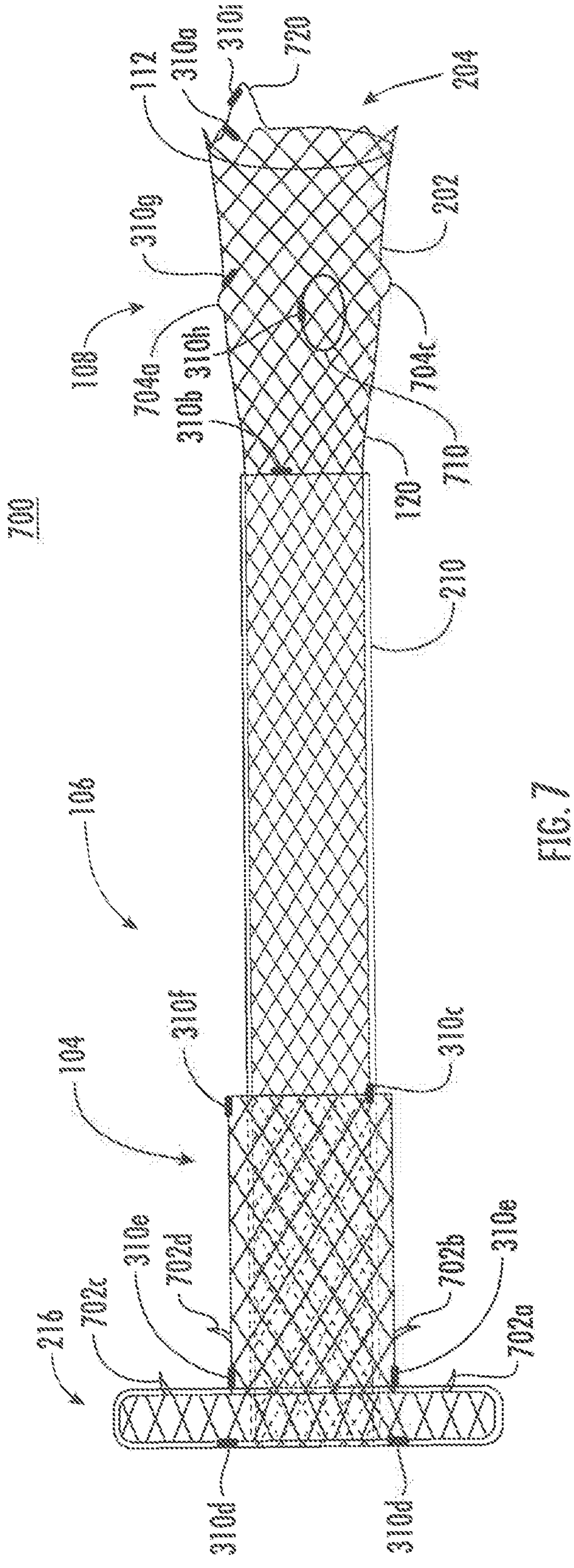
FIG. 7 illustrates a perspective view of a medical device with several imageable markers and retention features, according to at least one embodiment of the present disclosure.

Second end portion 108 may comprise an additional retention member, such as flare 112 (or features as are illustrated in FIGS. 8A-8I), or second end portion 108 may comprise a straight edge such as illustrated with respect to second portion 224 of FIG. 2B. Embodiments are not limited in this context. Second end portion 108 may also comprise filament ends 130 which are finished or unfinished. For example, filament ends 130 may be welded together, continuously formed, connected via a circumferential ring (as shown in FIG. 7), glued, or otherwise finished, or they may be frayed, unconnected, or otherwise unfinished (not illustrated). In several embodiments, filament ends 130 may be arranged such that the second end portion 108 has a diameter "D4" that is larger than a diameter D1 of a central portion of the elongate tubular body 118, as shown in FIG. 1A. In other embodiments, filament ends may be configured such that diameter D4 of second end portion 108 may be substantially the same as the diameter D1 of the central portion 118. Alternatively and/or additionally, the filament ends may turn or curve radially inward so that diameter D4 is less than diameter D1 of the central portion 118. It will be recognized that radially outward extending filament ends 130 may increase trauma to a surrounding tissue (not illustrated), which may enhance tissue growth into the second end portion 108. It will be further recognized that radially inwardly extending filament ends 130 may decrease trauma to a surrounding tissue (not illustrated), which may reduce discomfort for and/or infection risk for a patient.

Referring to FIG. 1A, retention member 216 may be characterized by axial length L1 and overlap portion 104 may be characterized by an axial length "L2." Central portion 106 may be characterized by an axial length L3 and second end portion 108 may be characterized by an axial length L4. In many embodiments, L1 may be less than L4. L2 and L3 may together have a length sufficient to span a distance between a first body lumen and a second body lumen (not illustrated), or L2 alone may be sufficient to span a distance between a first body lumen and a second body lumen. In some embodiments, L2 may be less than, equal to, or greater than L3. For example, L2 may be 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300% of L3. In some embodiments, L2 may be greater than 300% of L3. In one non-limiting example, L3 may be 0 mm (e.g., overlap portion 104 may extend an entire length between retention member 216 and second end portion 108). In many embodiments, L2 may be at least 30%, 40%, 50%, 60%, 70%, or 80% of a full length of the medical device 100 (e.g., L1+L2+L3+L4).

In many embodiments, cover 210 may have lengths of L3, L2+L3, L1+L2+L3. In some embodiments cover 210 may have a length of L1+×L2+L3, wherein x represents a value between 1 and 2 such that cover 210 extends beyond retention member 216 along radially outer wall 126 (not illustrated). It is presently contemplated that a cover may extend along a greater portion of the total length of an elongate body 118 used to form a medical device 100 with a doubled-back design. For example, cover 210 may extend along a full length of medical device 100, with a length of L1+L2+L3+L4, along a full length of medical device 100 including a doubled-back length extending around retention member 216 and along radially outer wall 126, with a length of L2+L1+L1+L2+L3+L4, or a length between such, in which cover 210 is aligned with second end portion 108. In many embodiments, a full length of medical device 100 may comprise L1, L2, L3, and L4 and be 5-20 cm, or any iterative range therein inclusive of 0.1 cm increments, including but not limited to 6-12 cm, 8-10 cm, 10-15 cm, 8-12 cm, etc. In some nonlimiting embodiments, medical device 100 may have a full length up to 25 cm.

Elongate tubular body 118 may define a diameter "D1." D1 may be greater in the second configuration than in the first configuration. In many embodiments, central portion 108, radially inner wall 124, or both may have a diameter D1. Radially outer wall 126 may have a diameter "D2," which is greater than D1. Retention member 216 may have a diameter "D3" which is greater than D2. For example, D3 may be 1.5, 2, or 2.5 times D1 or D2. In various embodiments, D3 may be 5-35 mm, or any iterative range therein inclusive of 0.1 mm increments, including but not limited to 6-12 mm, 8-10 mm, 10-15 mm, 8-12 mm, etc. In some embodiments, second end portion 108 may comprise diameter D4 which is greater than D1. In some embodiments, D4 may be equal to or greater than D1, D4 may be equal to or greater than D2, or equal to or greater than D3.

FIGS. 2A-2B illustrate a fully extended (e.g., unfolded, straightened) elongate body 200 which is suitable for being inverted (e.g., folded, doubled back, reconfigured), either fully or partially, to form medical device 214. Medical device 214 may comprise one or more similarities to medical device 100, as discussed with respect to FIGS. 1A-B. For example, medical device 214 may have a first configuration (e.g., constrained, unexpanded, delivery configuration, etc.) and a second configuration (e.g., unconstrained, expanded, deployed configuration, etc.). Embodiments are not limited in this context.

With respect to FIG. 2A, elongate body 200 may be formed of a woven filament 120 (FIG. 1A) and may define a lumen 204 extending longitudinally therethrough. Elongate body 200 may comprise a first uncovered portion 206, a second covered portion 208 comprising a cover 210, and a third uncovered portion 212. In the illustrated embodiment, second covered portion 208 is disposed between the first and second uncovered portions 206, 212.

Elongate body 200 may be inverted, folded, doubled back, or otherwise reconfigured to assume the shape of medical device 214. For example, in some embodiments, first uncovered portion 206 and at least part of second covered portion 208 may be doubled back and pulled through lumen 204 so as to extend through third uncovered portion 212.

In other embodiments, third uncovered portion 212 may be pulled around, or doubled back about, an exterior of second covered portion 208 so that first uncovered portion 206 and at least part of second covered portion 208 extend through third uncovered portion 212. In other words, third uncovered portion 212 may be doubled back or folded back along an outer surface of the second covered portion 208 so as to extend towards the first uncovered portion 206. The third uncovered portion 212 may be doubled back to form a retention member, for example, a retention member 216, around an outer diameter of the second covered portion 208. Accordingly, filament ends 130 as described with respect to FIG. 1A may no longer located at an end of the medical device structure, but wrapped away from a first wall 122 as described with respect to FIG. 1A or lip 630 as described with respect to FIG. 6, which may form the first end of the medical device 214. In other words, a doubled back end of elongate body 200 may extend beyond retention member 216 along the elongate body towards the opposing or opposite portion, which may form or otherwise include an opposing flange or other retention member. That is, the elongate body 200 may extend axially outward beyond retention member 216 such that a respective end is doubled back into the retention member 216.

In either case, medical device 214 may comprise a first portion 220 (e.g., proximal portion) and a second portion 224 (e.g., distal portion), each of which can include at least a partially uncovered radially outer surface (e.g., surface 226 of first portion 220 and surface 228 of portion 224). A central portion 222 (e.g., central saddle portion or region) may extend between first portion 220 and second portion 224. In many embodiments, central portion 222 may be fully or partially covered with cover 210. It will be recognized that surface 226 may correspond to third uncovered portion 212 as a result of the doubling back of elongate body 200. Surface 226 may be or comprise an uncovered segment of overlap portion 104 as described with respect to FIGS. 1A-1B, extending radially outward of the cover 210.

In many embodiments, first portion 220 may comprise a retention member 216 (e.g., flange, double-walled flange). Retention member 216 can be formed with part of the doubled-back elongate body 200 such that inner layer 230 extends radially inward to separate lumen 204 from the retention member 216 structure. Inner layer 230 may comprise cover 210, which may limit impaction or lodging of material, such as chyme, within an interior of the retention member 216 and/or unwanted fluid leakage radially outward through the structure of retention member 216. Portion 218 refers to the covered portion of medical device 214 extending longitudinally from retention member 216. Portion 218 may include part or all of a portion of medical device 214 formed from second covered portion 208, such as inner layer 232 of first portion 220 or inner layer 232 with central portion 222. In many embodiments, surface 226 may have a shorter axial (longitudinal) length than portion 218. Accordingly, cover 210 may extend beyond the first end portion 104 as described with respect to FIGS. 1A-1B, towards the second end portion along a partial axial length of the medical device 100, 214.

It will be understood that various dimensions of elongate body 200 may correspond with respective dimensions of medical device 214. In many cases, dimensions of elongate body 200 may be the same or approximately linearly related to corresponding dimensions of medical device 214. Length "L9a" of third uncovered portion 212 may correspond with length "L9b" of surface 226. Length "L10a" along second covered portion 208 may correspond with length "L10b," the longitudinal or axial length of inner layer 230 of retention member 216. In many embodiments, L10b may be less than L10a to accommodate for a curvature, fold, or other projection of retention member 216. Length "Lila" along second covered portion 208 may correspond with length "L11b" of combined inner layer 230 and portion 218. Length "L12a" of first uncovered portion 206 may correspond with length "L12b" of second portion 224. It will be appreciated that these dimensional relationships are merely exemplary, and that others are contemplated.

Lumen 204 may have a diameter "D5a" in the first configuration of elongate body 200 and diameter "D5b" in the second configuration (e.g., deployed, doubled-back, expanded configuration) of medical device 214. D5b may be larger than D5a in many embodiments, for example, 100-700% the length of D5a, and in several embodiments, 500% the length of D5a. Surface 226 may have a larger diameter "D6" than inner layer 232 (D5b with the associated thickness of the inner layer 232, not labeled for the sake of simplicity in the drawings), which may allow for tissue ingrowth of surface 226. Retention member 216 may have a larger radial diameter D7 than D6. In some embodiments, D7 may be 100-300% the length of D6, such as 200%.

Elongate body 200 may represent medical device 214 in the first configuration. In this case, longitudinal or axial lengths L9a, L11a, and L12a may linearly or approximately linearly decrease in length to L9b, L11b, and L12b respectively with a deployment and/or expansion of medical device 214 to the second configuration.

It will be understood that components described with respect to FIGS. 1A-1B and FIGS. 2A-2B may be corresponding, interchangeable, or otherwise combinable. For example, retention member 216 as described with respect to FIG. 1A may have a greater diameter D7 than D6 of surface 226, creating second wall 128 with a sufficient diameter to effectively appose a tissue wall. Embodiments are not limited in this context.

Figure 3A:
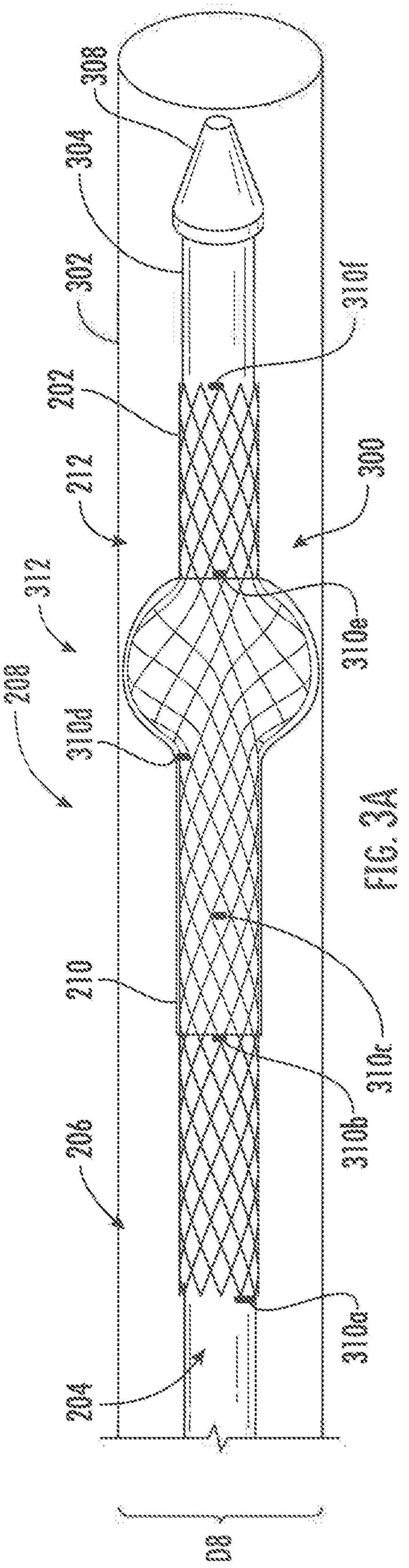
FIGS. 3A-3C illustrate side views of a medical device in a delivery configuration, according to various embodiments of the present disclosure.
Figure 3B:
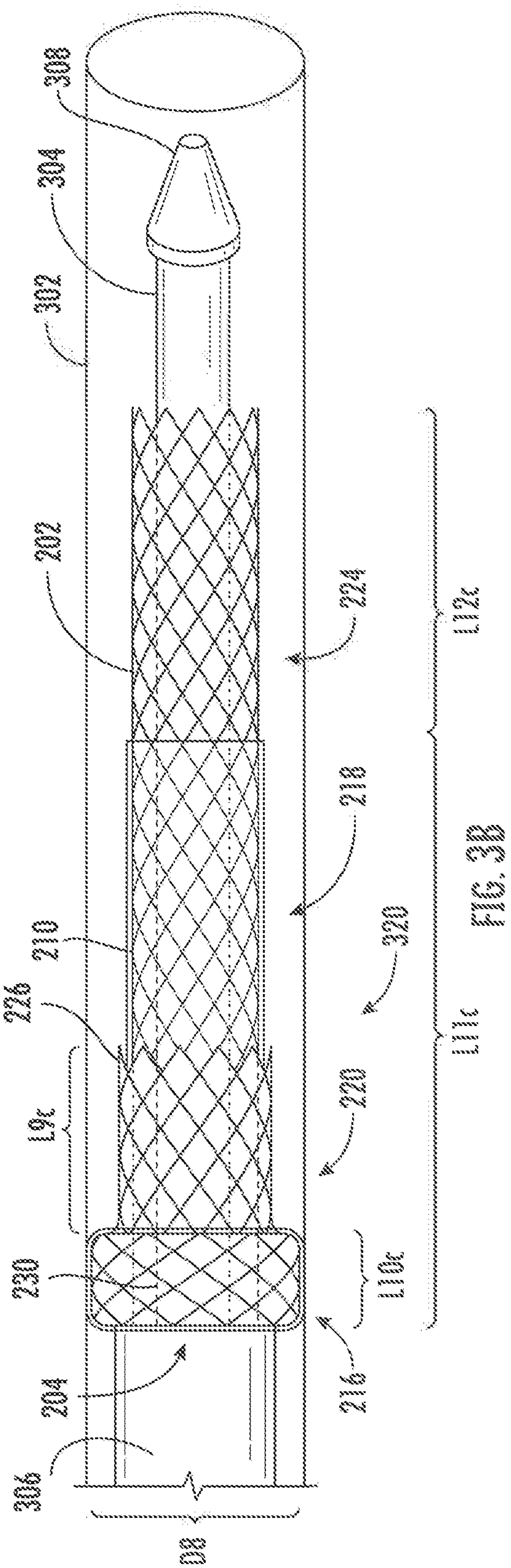
Figure 3C:
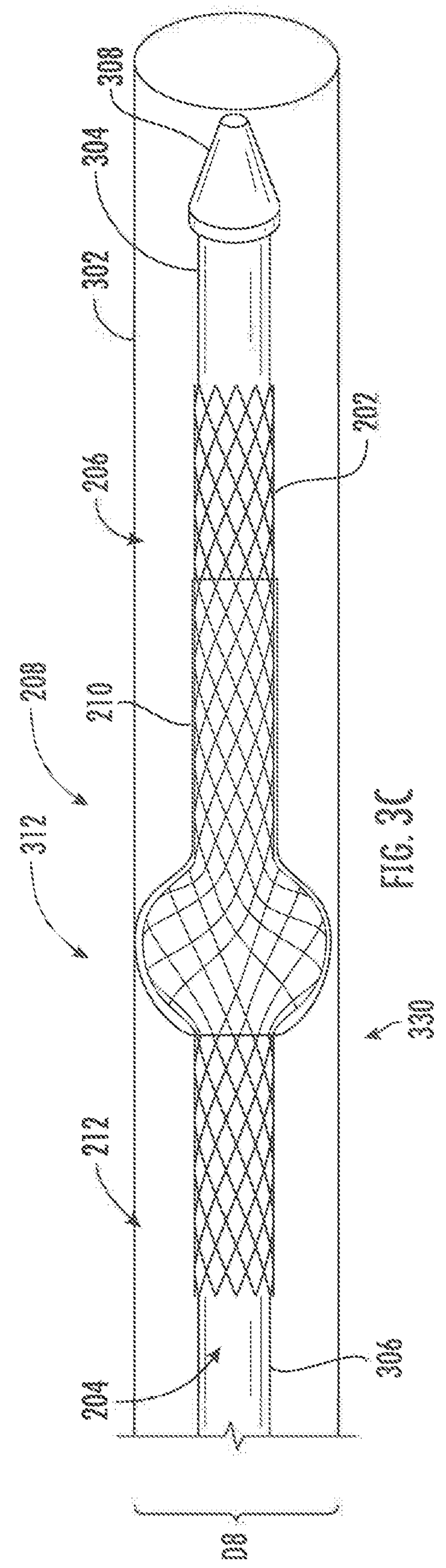

FIGS. 3A-3C present medical devices (e.g., stents) according to the present disclosure in various deployment configurations and within deployment tubes (e.g., catheters, sheaths, etc.) according to the present disclosure. In many embodiments the medical devices are formed from shape memory or other appropriate material such that they can be delivered to a target location within a patient in a compressed configuration. When deployed at the target location, the medical devices can return to the pre-shaped configuration to engage patient tissue in a desired manner. Thus, medical devices as described with respect to FIGS. 2A-3C may be delivered in presently described constrained configurations to a position of interest (e.g., in body lumen(s), not shown). In some embodiments, the medical devices may adopt an elongated configuration in which, in some or all of the geometric features of the medical device are compressed, longitudinally extended, unfolded, or otherwise adjusted to enable the medical device to be accommodated within the deployment tube. Deployment of the medical devices of FIGS. 3A-3C (e.g., releasing from constraint, expansion, etc., such as by retracting the deployment tube from around the medical device) may cause the respective medical devices to adopt an unconstrained (e.g., expanded, etc.) configuration as shown in FIGS. 1A-B and/or FIG. 2B (e.g., to return to a predetermined heat-set shape). Each of FIGS. 3A-3C is illustrated with various elements as described with respect to FIGS. 2A-2B for the sake of simplicity, but it will be understood that deployment configurations may similarly apply to medical device 100 as described above, and/or that medical devices illustrated presently may alternatively include one or more elements as described with respect to FIGS. 1A-1B. Embodiments are not limited in this context.

Each of the medical devices 300, 320, 330 is illustrated within an outer sheath 302 (e.g., tube, catheter, delivery sheath, etc.) which can be used to deploy the medical devices. In many embodiments, an inner member 304 may extend through a lumen 204 of the medical device 300, 320, 330. The inner member 303 may include a tip 308 disposed (e.g., distally disposed) thereon. Tip 308 may be and/or may otherwise comprise a cutting element, for example, a knife, electrocautery tip, or other cutting element capable of piercing tissue (not illustrated). In various embodiments, outer sheath 302 and inner member 304 may be independently retractable and/or extendable with respect to each other. Outer sheath 302 and inner member 304 may be locked to a position relative to each other and/or with respect to a handle of a delivery device (not shown). Some embodiments may comprise a separate pusher 306, which may be used to manipulate medical device 300, 320, 330 during and/or upon its deployment. Pusher 306 may be separate from inner member 304, may be circumferentially disposed about inner member 304, or may otherwise be positioned within outer sheath 302. Pusher 306 may be independently retractable, extendable, and/or lockable with respect to either or both of outer sheath 302 and inner member 304. Various embodiments may comprise only one of inner member 304 or pusher 306.

In some embodiments, the outer sheath 302 may be retracted with respect to the inner member 304, causing the medical device 300, 320, 330 to be unconstrained, and thus the distal portion of the medical device 300, 320, 330 may automatically radially or otherwise expand (e.g., to assume a heat-set shape of woven filament 202).

In some embodiments, it may be desirable to recapture the medical device after it has been partially or completely deployed. In such instances, outer sheath 302 may be distally advanced with respect to the inner member 304, causing a deployed and/or partially deployed medical device 300, 320, 330 to be reconstrained and/or recaptured by the distal end of the outer sheath 302. When the medical device 300, 320, 330 is reconstrained by the distal end of the outer sheath 302 (e.g., by distally extending the outer sheath 302 longitudinally over the medical device 300, 320, 330), the distal portion of the medical device 300, 320, 330 may radially contract from a deployed (uncompressed, expanded) configuration to a constrained (e.g., compressed, unexpanded, etc.) configuration. Recapture of a medical device 300, 320, 330 may enable reorientation and proper redeployment of the medical device 300, 320, 330 in the case of improper alignment.

In some embodiments the doubled-back (e.g., unconstrained, expanded, folded, etc.) configuration of various medical devices of the present disclosure may be automatically formed by the medical device within a body lumen when the medical device is deployed. Referring to FIG. 3A, medical device 300 may be a stent such as described with respect to medical device 214. Medical device 300 may be deployed in a first constrained (e.g., compressed, unexpanded, etc.) configuration to a desired position (e.g., in a body lumen, not shown). Owing to the shape recovery feature of the medical device 300, first uncovered portion 206 and second covered portion 208 may be configured to automatically invert, upon deployment, through lumen 204 so as to extend through third uncovered portion 212 in the second configuration, thus forming the shape of the unconstrained configuration as shown in FIG. 2B. Third uncovered portion 212 may thus form surface 226, as described with respect to FIGS. 2A-2B.

It will be recognized that inner member 304 may prevent inversion and/or transition of medical device 300 to the second configuration when medical device 300 is disposed about the inner member. Retraction of inner member 304 (e.g., proximal retraction) may facilitate movement of the medical device 300 to the second configuration. In many embodiments, outer sheath 302 may be (proximally) withdrawn with respect to inner member 304 and medical device 300 prior to withdrawal or retraction of inner member 304 with respect to medical device 300.

In some embodiments, a portion of a medical device configured to form a retention member may be either partially or completely straightened or extended when the medical device is in the first configuration (e.g., woven filament 202, which has been preset to form retention member 216, may resist conforming to a constrained configuration that is perfectly straight, and thus a bulge 312 may exist in the constrained configuration of a medical device 300, 330 as shown in FIG. 3A. For example, bulge 312 may correspond to a portion of medical device 300 which will form retention member 216 when the medical device is unconstrained from outer sheath 302 and/or released from inner member 304 (e.g., via proximal retraction of one or both of outer sheath 302 and inner member 304).

Medical device 300 may, in some embodiments, include one or more imageable markers 310*a-f* in order to facilitate visualization of a desired placement of the medical device in one or more body lumens. One or more of imageable markers 310*a-f* may be echogenic, radiopaque, colored, visual, or otherwise viewable. Imageable markers 310*a-f* may be placed along medical device 300 along positions of interest thereof. Imageable markers may be embedded in a cover 210, integrated with a woven filament 120, or otherwise coupled to medical device 300.

For example, imageable marker 310*a* marks a proximal end of medical device 300 in the first configuration and a distal end of medical device 300 in the second configuration (not shown). Imageable marker 310*b* marks a proximal end of cover 210 in the first configuration and a distal end of cover 210 (e.g., a distal end of portion 218) in the second configuration. Imageable marker 310*c* marks a position along second covered portion 208 which will correspond to a distal end of third uncovered portion 212 (e.g., as surface 226) when medical device 300 moves to the second configuration. Imageable marker 310*d* marks a position along second covered portion 208 which will correspond to a proximal end of a retention member when medical device 300 moves to the second configuration. Imageable marker 310*e* marks a position along second covered portion 208 which will correspond to a distal end of a retention member when medical device 300 moves to the second configuration. For example, when medical device 300 is the same as medical device 100, imageable marker 310*d* may mark a position along the second uncovered portion 208 which corresponds to first wall 122 when in the second configuration, and imageable marker 310*e* may mark a position which corresponds to second wall 128. Imageable marker 310*e* may additionally, or alternatively, correspond to an end of cover 210, which may be a distal end when medical device 300 is in the first configuration. When medical device 300 is in the second configuration, imageable marker 310*e* may mark a proximal end of cover 210, which may be wrapped (e.g., doubled-back, folded, etc.) at least partially around a retention member, as described with respect to cover 210 and retention member 216 with respect to FIGS. 1A-1B. Imageable marker 310*f* marks a distal end of medical device 300 in the first configuration and an end of a doubled-back portion (e.g., surface 226) when medical device 300 is in the second configuration (not shown). As illustrated, imageable markers 310*c* and 310*f* may align in the second configuration (not shown).

It will be understood that imageable markers 310*a-f* may be positioned as illustrated and/or elsewhere along medical device 300 where useful for deployment and/or visualization of medical device 300 in either or both first and second configurations, for example, as described above. Medical device 300 may comprise 6 imageable markers, as described above, or medical device 300 may comprise more or fewer imageable markers. Medical professionals may image one or more such markers discontinuously (e.g., via still frames) on continuously (e.g., via ultrasound feed). Relative position and/or motion of any of the imageable markers 310*a-f* as described above may be used to determine a placement, position, and/or completion of deployment of medical device 300, for example, with respect to another element of medical device 300 and/or with respect to another of the imageable markers 310*a-f*. Additionally, while not illustrated for the sake of simplicity, one or more of medical devices 100, 320, 330 or medical device 214 may comprise at least one of imageable markers 310*a-f* as described above.

As will be appreciated, for purposes of deploying medical device 300 to engage one or more body lumens, medical device may be radially squeezed, axially unfolded, compressed, or otherwise deformed in order to fit into outer sheath 302, which may have a diameter "D8." For example, when medical device 300 comprises dimensions as discussed with respect to medical device 214 when in the second configuration, D8 may be less than corresponding diameter D7 of retention member 216, less than D6, and/or less than D5b. In many embodiments, D8 may be less than D5a, which may correspond to an elongate body 200 which is not compressed to fit within outer sheath 302.

FIG. 3B illustrates a first configuration of medical device 320 according to embodiments described herein. Medical device 320 may be a stent such as described with respect to medical device 214, wherein portion 218 and second portion 224 extend through surface 226. As will be appreciated, the first configuration of medical device 320 illustrated in FIG. 3B does not allow an inversion or doubling back of medical device 320 between first and second configurations. Rather, medical device 320 is, in this embodiment, loaded into outer sheath 302 pre-shaped with a doubled-back configuration.

Medical device 320 may be radially squeezed, compressed, or otherwise deformed in order to fit into outer sheath 302, which may have diameter D8. For example, when medical device 320 comprises dimensions as discussed with respect to medical device 214 when in the second configuration, D8 may be less than corresponding diameter D7 of retention member 216, less than D6, and/or less than D5b.

Loading of medical device 300, 320, 330 into outer sheath 302 may result in a longitudinal extension of the same. In particular, one or more elements may assume a longer length in the first configuration than in the second configuration. For example, with respect to medical device 320, which may be a medical device 214 with a pre-doubled-back first configuration, surface 226 may have a length "L9c" which is longitudinally/axially longer than L9b. Retention member 216 may comprise a length "L10c" which is longitudinally/axially longer than L10b as discussed with respect to FIG. 2B. Inner layer 230 and portion 218 may together have a length "L11c" in the first configuration which is longitudinally/axially longer than L11b. Second portion 224 may have a length "L12c" which is longitudinally/axially longer than L12b. While not illustrated in FIGS. 3A and 3C for the sake of simplicity of the drawings, it is presently contemplated that medical device 300, 330 may comprise dimensions similarly corresponding to dimensions described with respect to FIGS. 2A-2B, but which have been respectively radially compressed or longitudinally expanded.

Referring now to FIG. 3C, medical device 330 may be configured to adopt a doubled-back shape upon its deployment. For example, as previously described, medical device 300 may be delivered in a disassembled, straightened, unfolded, etc. configuration and may then be allowed to reassemble, double back, fold, etc. to a preset shape (e.g., heat set shape) upon deployment. Medical device 300 may comprise one or more similarities to medical device 214 in the second configuration. However, in contrast to medical device 214, upon deployment medical device 330 may double back (e.g., fold, reassemble) employing a radially outward folding mechanism as opposed to the inward inversion associated with medical device 214. For example, third uncovered portion 212 may be configured to outwardly fold along bulge 312 when unconstrained from outer sheath 302. Medical device 330 may convert from the first configuration to the second configuration by doubling back (e.g., folding over, inverting, etc.) first uncovered portion 206 (or the first uncovered portion 206 together with part of second covered portion 208) over at least part of second covered portion 208. Accordingly, medical device 330 may comprise a second configuration with one or more similarities to medical device 214. Third uncovered portion 212, in a first configuration as illustrated in FIG. 3C may, for example, correspond in the second configuration to surface 226 described with respect to FIG. 2B, while first uncovered portion 206, in the first configuration of FIG. 3C, may correspond in the second configuration to second portion 224 as described with respect to FIG. 2B.

Similarly, as described with respect to FIG. 3A, bulge 312 may correspond to a portion of medical device 330 which will form a retention member such as retention member 216 when the medical device 330 is fully unconstrained from outer sheath 302 and/or released from inner member 304 (e.g., via proximal retraction of one or both of outer sheath 302 and inner member 304).

Figure 4A:
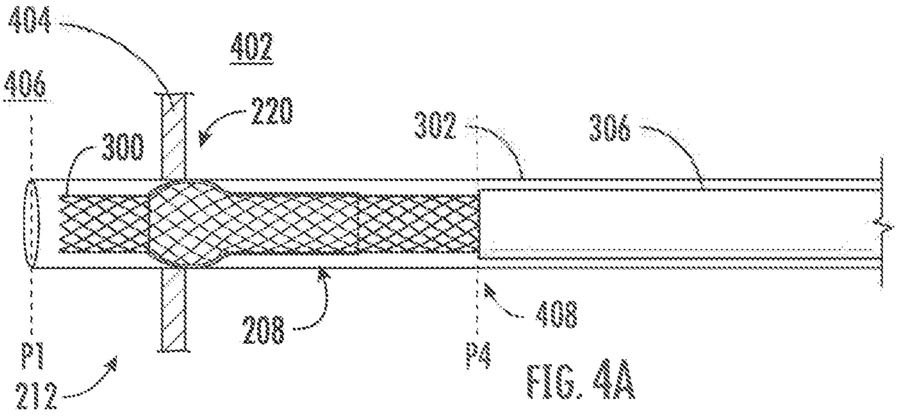
FIGS. 4A-4F illustrate side views of a medical device delivery sequence, according to various embodiments of the present disclosure.
Figure 4B:
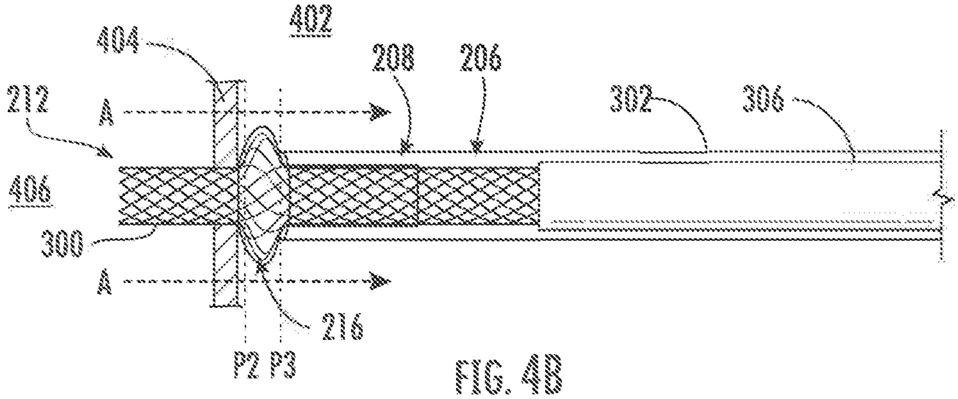
Figure 4C:
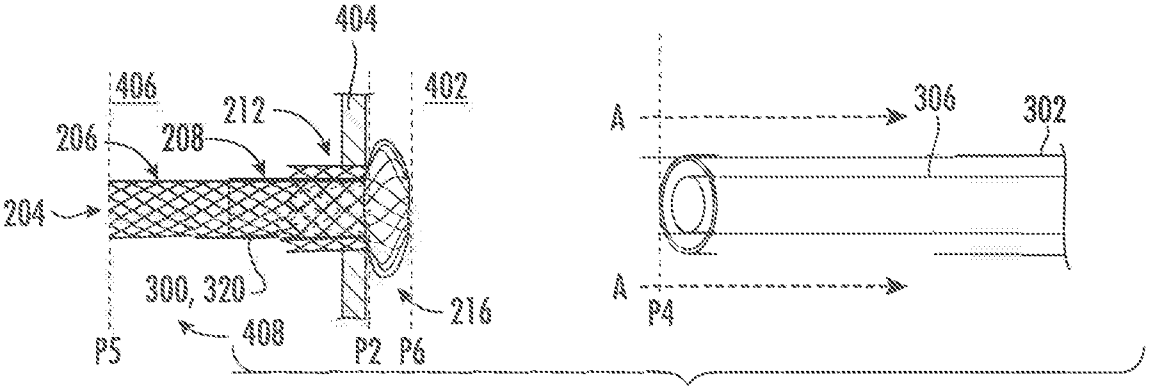
Figure 4D:
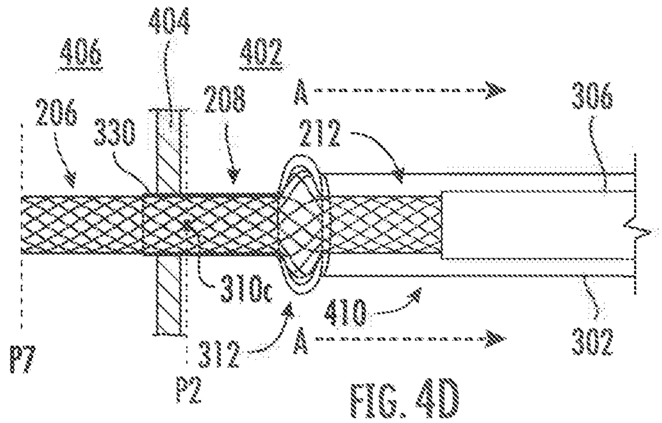
Figure 4E:
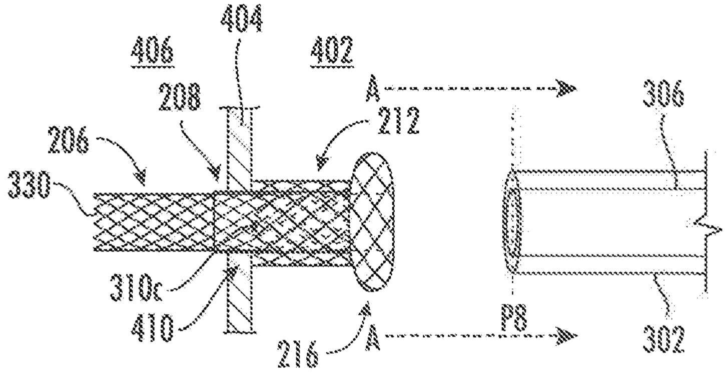
Figure 4F:
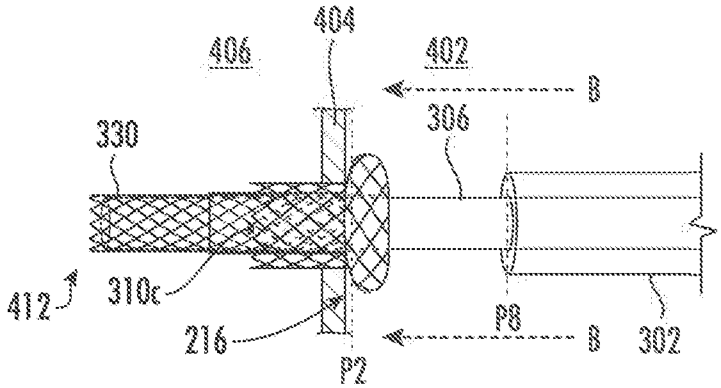

FIGS. 4A-4F illustrate various deployment stages of medical devices described herein, which relate to methods for delivering medical devices having various constrained configurations as described in FIGS. 3A-3C, to target locations within the body whereupon the medical devices can be deployed to adopt delivery (e.g., unconstrained) configurations as described with respect to FIGS. 1A-B and/or FIG. 2B. In particular, FIGS. 4A-4C illustrate a non-limiting example method for deploying medical device 300 (FIG. 3A). FIG. 4C may additionally, or alternatively, illustrate deployment of medical device 320 (FIG. 3B). FIGS. 4D-4F may relate to deployment of medical device 330 (FIG. 3C) as described above. FIGS. 4A-4F make reference to one or more elements as described above, for the sake of simplicity. It will be understood that any of the referenced elements or combinations thereof may be alternatively configured. Embodiments are not limited in this context.

FIG. 4A relates to a first step or stage of a delivery of medical device 300 as described above with respect to FIG. 3A. In FIG. 4A, medical device 300 is shown in an elongated, radially compressed configuration within outer sheath 302. In this configuration, the outer sheath 302 and medical device 300 may be positioned within body lumens 402, 406 for a desired deployment. In particular, distal tip 308 and/or inner member 304 may form an opening in tissue wall 404 between body lumens 402, 406. Part of outer sheath 302 containing medical device 300 disposed therein may be advanced (e.g., distally advanced or extended) from first body lumen 402 across tissue wall 404 so that a distal end of the outer sheath 302 assumes a position "P1" within second body lumen 406.

It is noted that FIG. 4A does not illustrate an inner member 304, but rather a pusher 306 which is configured to couple with or otherwise support an end 408 (e.g., proximal end or first end) of medical device 300 so as to prevent pre-deployment movement of medical device 300 from the first configuration toward the second configuration. It will be understood that, in various embodiments, inner member 304 may be used to form an opening in tissue wall 404 through which the outer sheath 320 and medical device 300 may be inserted. The inner member 304 may be retracted after medical device 300 is positioned across said opening.

FIG. 4B shows outer sheath 302 retracted in the direction of arrows "A" with respect to medical device 300 and pusher 306, to uncover a portion of the medical device 300. In the illustrated embodiment, third uncovered portion 212 of medical device 300, which spans the tissue wall 404, is uncovered. Accordingly, third uncovered portion 212 is partially positioned within second body lumen 406.

Outer sheath 302 may then be retracted such that the distal end of the outer sheath moves from first position P1 to a second position "P2." P2 may be a desired location for placement of a retention member of medical device 300, (e.g., second wall 128 shown in FIG. 1A). Thereafter, the outer sheath 302 may be retracted so that its distal end is located at a third position "P3." P3 may be to a position in the retention member (e.g., retention member 216 in FIG. 1C) reassumes its predetermined shape.

FIG. 4C illustrates a next stage of deployment of medical device 300 in which outer sheath 302 is further retracted in the direction of arrows "A" such that the distal end of the outer sheath moves to a fourth position "P4," such that the medical device 300 is fully released from the outer sheath. Such release may allow first uncovered portion 206 to completely assume its original preset shape, in the process of which it doubles back through third uncovered portion 212 so as to fully form retention member 216 and extend back into second body lumen 406, as shown in FIG. 4C. In the fully-unconstrained configuration, retention member 216 is positioned within first body lumen 402, third uncovered portion 212 spans tissue wall 404, third uncovered portion 212 corresponding to surface 226 as described with respect to FIG. 2B (not presently shown). First uncovered portion 206 is positioned within second body lumen 406, first uncovered portion 206 corresponding to second portion 224 as described with respect to FIG. 2B (not presently shown).

As previously mentioned, the medical devices according to the disclosure can be deployed to a target tissue site in any of a variety of configurations. The embodiment discussed in relation to FIGS. 4A-4C show deployment of a medical device 300 in which the retention member 216 is formed and portions of the device fold within other portions of the device as the device is being deployed. Alternatively, the medical device (e.g., medical device 320) can be formed and then simply compressed to fit within the outer sheath. That is, medical device 320 comprises a constrained configuration with a preassembled doubled-back shape, as shown in FIG. 3B. In this case, medical device 320 is positioned within outer sheath 302, and as shown in FIG. 4C is then distally extended through first body lumen 402 and into second body lumen 406 so that it spans tissue wall 404 until the outer sheath 302 and end 408 of medical device 320 are positioned at a position "P5" within second body lumen 406. The sheath 302 can then be retracted in the direction of arrows A until the distal end of the sheath 302 passes position "P6", at which point the sheath to releases (e.g., unconstrains) the medical device 320, fixing the device in the desired location.

It will be understood that the various positions described herein are merely exemplary, and that other positions may correspond with a desired placement and deployment of a medical device. For example, depending on the particular longitudinal/axial contraction of the medical device 320 when moving from the first configuration to the second configuration, P5 may be located more distal than a desired end placement of end 408 of the medical device 320 to ensure that when the medical device longitudinally/axially contracts (i.e., when the sheath 302 is removed, such contraction results in a desired alignment of end 408 within second body lumen 406.

FIGS. 4D-4F illustrate a non-limiting example method for deploying medical device 330 (FIG. 3C). As with prior embodiments, medical device 330 may have a constrained configuration with a disassembled (e.g., unfolded, stretched out, extended, etc.) shape which may then be deployed to adopt an unconstrained shape as shown in FIG. 2A. FIGS. 4D-4F illustrate an exemplary deployment of medical device 330 in which the third uncovered portion 212 outwardly folds about bulge 312 when deployed from the outer sheath 302 so as to adopt a shape as described with respect to FIG. 2A. This is in contrast to the deployment method discussed in relation to FIGS. 4A-4C in which a portion of the medical device 300 folds back within another portion in order to form the retention member.

Referring to FIG. 4D, a first stage of deployment of medical device 330 is shown. As shown, outer sheath 302 containing medical device 330 may be distally advanced so that a distal end of the medical device 330 achieves a position "P7" within second body lumen 406. In many embodiments, this positioning may be an amount that ensures that imageable marker 310*c* remains within the first body lumen 402. For example, medical device 320 may be distally advanced until imageable marker 310*a* reaches position P2, which may further correspond to an opening within tissue wall 404.

FIG. 4E shows a subsequent stage of deployment of medical device 330, in which outer sheath 302 may be proximally retracted in the direction of arrows A with respect to medical device 330. Outer sheath 302 may be retracted until the distal end of the outer sheath is located at a position "P8" such that end 410 of the medical device 330 is released from the outer sheath. Upon its release from sheath 302, end 408 may move to the second, unconstrained, configuration shown in FIG. 4E. As can be seen, when end 408 is released from the outer sheath 308, it outwardly doubles back over second covered portion 208 so that end 408 lies directly adjacent to the tissue wall 404.

FIG. 4F illustrates a final stage of deployment and/or positioning of medical device 330 in which pusher 306 is distally extended in the direction of arrows B and is used to push or otherwise move medical device 330 to a desired position with respect to tissue wall 404. In the illustrated embodiment, the pusher 306 is used to position retention member 216 at position P2, directly adjacent to, and in contact with, tissue wall 404. In some embodiments, pusher 306 may manipulate medical device 330 by extending through lumen 204 of medical device 330 and coupling with an end 412 of medical device 330, for example, via a grasper (not shown). Alternatively, pusher 306 may apply pressure to a retention member 216 or other element of medical device 330 in order to move medical device 330 to a desired alignment (method not shown).

It will be understood that positioning of elements as described with respect to FIGS. 4A-4F may, in many cases, be based on imaging one or more imageable markers 310*a-f*, as described with respect to FIG. 3A. For example, while only imageable marker 310*c* is illustrated in FIGS. 4A-4F for the sake of simplicity in the drawings, imageable marker 310*e* may be positioned at P2 to determine appropriate medical device placement as described with respect to FIG. 4B. With respect to FIG. 4F, medical device 330 may be distally moved via pusher 306 until imageable marker 310*d* is positioned at P2.

While FIGS. 4A-4F illustrate medical device 300, 320, 330 (as described above) as spanning single tissue wall 404, presently disclosed embodiments may be additionally or alternatively be advantageous for placement across multiple walls. In some embodiments, devices with presently disclosed doubled-back designs may be suitable for spanning intermediate body lumens between first and second body lumens. For example, FIG. 5 illustrates medical device 100, 214, 300, 320, 330 positioned across first body lumen 502, second body lumen 504 (e.g., intermediate body lumen), and third body lumen 506. In some examples, such as in HGS procedures, first body lumen 502 may be a gastric zone, second body lumen 504 may be a peritoneal cavity, and third body lumen 506 may be a hepatic zone. However, other configurations are presently envisioned.

Medical device 100, 214, 300, 320, 330 may be positioned across multiple tissue layers, for example, first tissue layer 512 and second tissue layer 514. In many embodiments, an uncovered portion of medical device 100, 214, 300, 320, 330 may be positioned to appose each tissue layer spanned. For example, surface 226 may be configured such that length L9b spans first tissue layer 512 and second tissue layer 514, encouraging ingrowth of tissue into medical device 100, 214, 300, 320, 330 and improving retention strength over conventional covered stent designs. At the same time, the extension of length L11b of cover 210 across first and second tissue layers 512, 514, spanning second body lumen 504, establishes a leak-free fluid flow path between first and second body lumens 502, 506.

In some embodiments, first uncovered portion 206 may be positioned within a duct 508, enabling fluid flow between the duct 508 and first body lumen 502. One benefit of positioning the first uncovered portion 206 within third body lumen 506 and/or duct 508 may be to allow tissue in-growth into first uncovered portion 206, reducing risk of stent migration. An additional, or alternative, benefit of the positioning of first uncovered portion 206 within duct 508 may be to allow drainage to enter lumen 204 of the stent from one or more side ducts 510 positioned adjacent to first uncovered portion 206.

Figure 6:
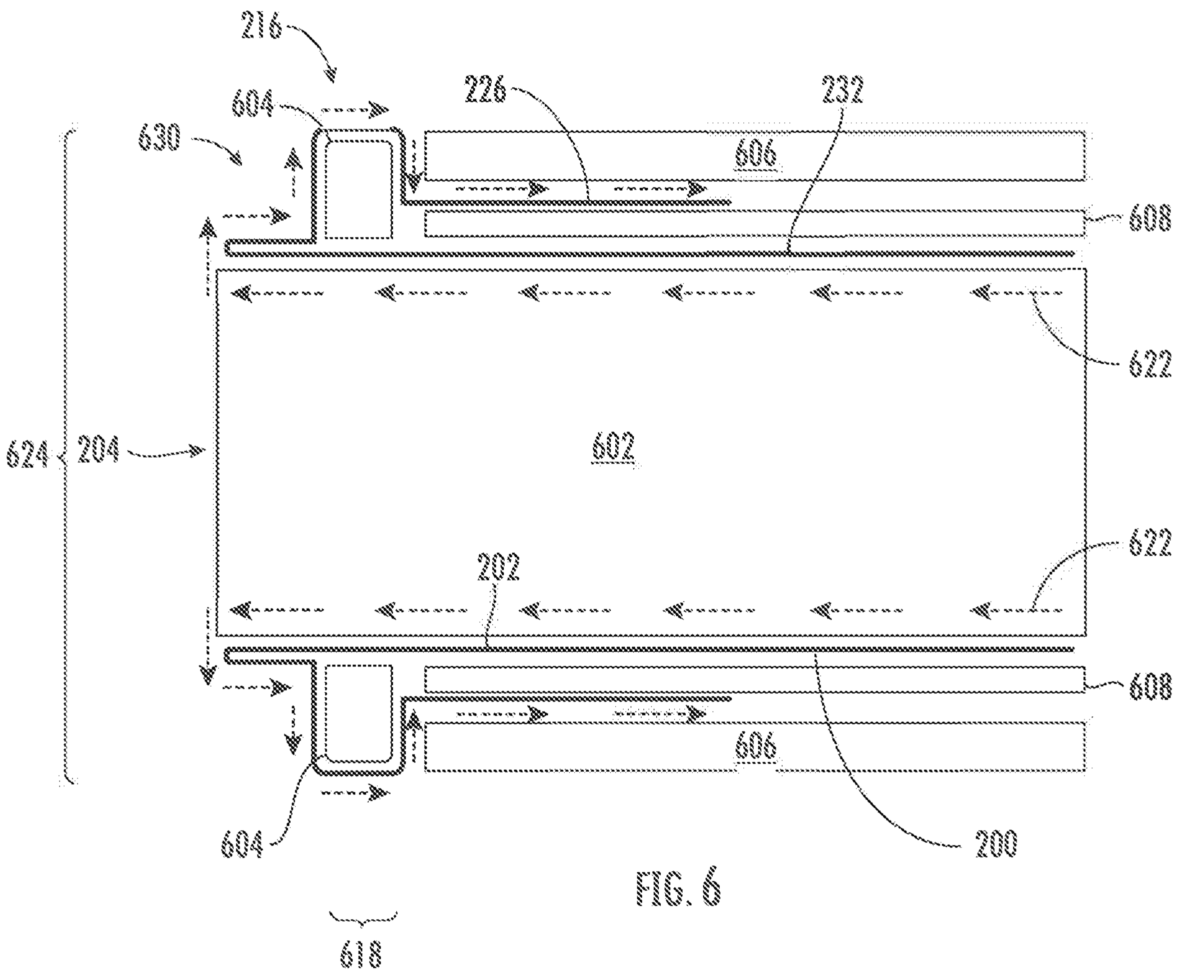
FIG. 6 illustrates a cross-sectional view of a medical device and a manufacturing system, according to at least one embodiment of the present disclosure.

FIG. 6 illustrates components and methods related to the manufacture of medical devices according to various embodiments described herein. For example, medical device 100, 214, 300, 320, 330 as described above may be manufactured to provide the features described with respect to FIG. 6. For the sake of simplicity, reference will be made in FIG. 6 to one or more components as described with respect to FIG. 2A-2B. However, embodiments are not limited in this context (e.g., features and/or methods described with respect to FIG. 6 may also be used to manufacture embodiments described with respect to FIGS. 7-8).

FIG. 6 illustrates a profile of an elongated body, such as elongated body 200 described above with respect to FIG. 2A, formed or placed around a mandrel 602. In many embodiments, the elongated body 200 may be formed with a woven filament 202 following a wire path as illustrated by dashed arrows 622. Embodiments are not limited in this context.

The mandrel 602 may accordingly set an inner diameter of lumen 204 extending through the elongated body 200. In many embodiments, the mandrel 602 may be cylindrical, though such is not critical and other shapes may be used. In some embodiments (not shown), mandrel 602 may comprise one or more surface variations so as to define elongate body 200 with a retention member such as a flare, bulge, or other surface feature, for example, as described with respect to FIGS. 8A-8I. Saddle clip 606 may extend partially or entirely around a circumference (not shown) of elongate body 200, in many cases including at least part of the doubled-back first portion 220 so as to constrain an outer diameter of the elongated body against mandrel 602.

In many embodiments, a retention member forming washer such as washer 604 may be placed or otherwise located around an outer circumference of the elongate body 200. In some embodiments (not illustrated), multiple washers 604 may be placed about elongate body 200, for example, to create a multi-flanged retention member or multiple retention members.

In many embodiments, a spacing clip 608 may be placed between saddle clip 606 and mandrel 602, and particularly between surface 226 and inner layer 232 as described above, to provide the difference in diameters D5b and D6 as referenced with respect to FIG. 2B.

Elongated body 200 may be doubled back over washer 604 so that a width 618 and diameter 624 of washer 604 may define a corresponding width and/or a diameter of a retention member. For example, third uncovered portion 212, as described with respect to FIG. 2A, of elongated body 200 may be doubled back over washer 604 so that width 618 of washer 604 defines length L10b and diameter 624 defines diameter D7 of retention member 216.

In some embodiments, elongate body 200 may be doubled back to include a protrusion or lip 630, which may extend from retention member 216 coaxially with inner layer 232. Lip 630 may be formed from an excess length of the portion of the elongate body 200 folded back to form retention member 216. Lip 630 may be useful for removal of a medical device, for example, by providing a place for a pusher or grasper to hold (not shown). Without wishing to be bound by any theory, a lip may increase a pullout force necessary to remove a medical device based on added contusions to a woven filament 202 shape which must be deformed to allow for displacement of the medical device.

After elongated body 200 has been doubled back as described above, the shape of the wire may be set, for example, in a first configuration (e.g., expanded, unconstrained configuration) of a self-expanding stent or body. For example, woven filament 202 may comprise a shape-memory material, such as Nitinol or a similar alloy. The shape may be set, for example, by heat-setting. It will be recognized that after heat-setting, woven filament 202 may retain sufficient flexibility to elastically manipulate the device's shape. Accordingly, after the shape of medical device 100, 214, 300, 320, 330 has been set, the mandrel 602, saddle clip 606, spacing clip 608, and/or washer 604 may be removed (e.g., spacing clip 608 and/or washer 604 may be removed by stretching the outer surface 226 and/or the inner layer 232 with respect to each other so as to enable spacing clip 608 and/or washer 604 to be slide out of the intervening space between them).

In many embodiments, cover 210 or other layer may be applied to the medical device before or after its doubling back on mandrel 602 (not shown). A cover may comprise, for example, silicone, other polymer material, or a combination thereof. For example, a cover may comprise polyurethane, polytetrafluoroethylene, polyvinylidene fluoride, an aromatic polycarbonate-based thermoplastic urethane, and/or another material, or the like. Cover 210 may be applied by dip coating, painting, spraying, other known deposition method, applying a sleeve, or a combination thereof.

FIG. 7 illustrates a medical device 700 with additional retention, drainage, and positioning features according to various embodiments described herein. For the sake of simplicity, various components of medical device 700 will be described with respect to above elements. It will be understood that embodiments may additionally or alternatively include other elements, and that medical device 100, 214, 300, 320, and/or 330 as described above may additionally include any combination of elements presently described with respect to FIG. 7. For example, medical device 700 is illustrated with a second end portion 108 including flare 112, but similar embodiments may alternatively include a second portion 224 with a straight profile, as previously described.

Various embodiments may include additional retention elements in locations configured to appose tissue (not presently shown), which may securely attach to the tissue or motivate a growth response in the tissue to support ingrowth. For example, outwardly projecting prongs 702*a-d* may be placed at any of a variety of locations along retention member 216, overlap portion 104, and/or surface 226, or elsewhere along medical devices of the present disclosure. Prongs 702*a-d* may attach to a respective surface (e.g., via weld, glue, or other coupling mechanism) and extend with a curve, straight edge, or other angle so as to traumatically interface with apposed tissue (not shown).

In other embodiments, uncovered portions at one or more locations of medical device 700 may include one or more raised braid segments 704*a-c*, which may be formed by loosening a braid or weave at a portion of medical device 700. Without wishing to be bound by any theory, raised braid segments 704*a-c* may irritate apposed tissue or cause minor abrasions of apposed tissue so as to cause a growth response of the tissue, which may then grow into the uncovered portion of medical device 700 and reduce migration risk after the medical device has been placed in or across one or more body lumens.

Embodiments disclosed herein may also include one or more additional drainage features, such as window 710. Window 710 may accommodate, for example, drainage from a side duct 510 as discussed with respect to FIG. 5. Window 710 may be formed by a separation or widening in a pattern, braid, weave, or pitch of woven filament 202, laser cutting, other incision, incorporation of bounding frame (not shown), or other method. It will be appreciated that any number of windows 710, of any size and/or shape, can be used, and can be disposed in any desirable portion of the medical device 100, 214, 300, 320, 330, and 700. While window 710 is illustrated as revealing a braid of the back side of medical device 700, in other embodiments, windows 710 may be aligned with each other to provide full or partial flow paths transverse to the lumen 204 (not shown).

In some embodiments, at least one positioning feature 720 may be included in medical devices 100, 214, 300, 320, 330, and 700 according to the illustration provided with medical device 700. In the illustrated embodiment positioning feature 720 is an extending loop which may be integrally formed by woven filament 202 or otherwise coupled to medical device 700. Positioning feature 720 is illustrated as extending axially from second end portion 108, but the same or similar positioning features may be additionally or alternatively located along the medical device 700 structure to aid in positioning of the medical device 700 in tissue. For example, positioning feature 720 may enable a pusher 306 (or other device) as discussed with respect to FIGS. 3A-3F to couple to a medical device 300, 320, 330 to enable manipulation, repositioning, and/or removal of the medical device using the pusher or other device.

One or more of the aforementioned retention, drainage, or positioning features may be marked with an imageable marker, as described above. For example, in addition to or alternative to any previously discussed imageable markers 310*a-f*, imageable marker 310*g* may indicate a location of extending filament piece 704*a* under fluoroscopic or other imaging techniques. Window 710 may be marked with at least one imageable marker 310*h*, and/or positioning feature 720 may be marked with at least one imageable marker 310*i*.

Referring to FIGS. 8A-8G, in various embodiments, any of the medical devices 100, 214, 300, 320, 330, and/or 700 of the present disclosure may include a second retention member, such as one or more surface features (e.g., anti-migration surface features) disposed along an outer surface of the medical device and configured to atraumatically engage an inner wall of the second body lumen. For example, surface features as described herein may replace or be positioned in addition to flare 112 of second end portion 108 as described with respect to FIGS. 1A-1B or second portion 224 as described with respect to FIGS. 2A-2B. In other embodiments, surface features may be positioned along portion 218 as described with respect to FIGS. 2A-2B. In various embodiments, such surface features may be integrally formed from the one or more woven, braided and/or knitted filaments which form the elongate body 200. In addition, or alternatively, such surface features may be attached or otherwise secured to the woven, braided and/or knitted filament(s), or the cover, of the medical device, e.g., using a suitable weld, solder, glue, adhesive, resin or other bonding technique, as are commonly known in the art.

Figure 8A:
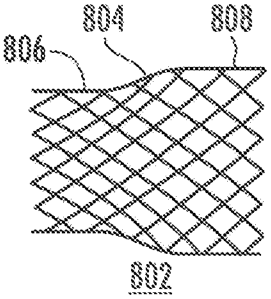
FIGS. 8A-8I illustrates side views of various retention features of a medical device, according to various embodiments of the present disclosure.

Referring to FIG. 8A, in one embodiment, a surface feature 802 may include a radial step 804 from a first portion 806 to a second portion 808, where the second portion has a larger diameter than first portion 806. Step 804 may extend around a full circumference of a presently described medical device, or it may extend around only a portion of the circumference.

Figure 8B:
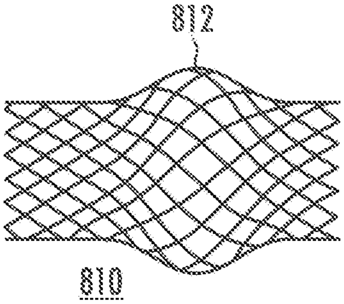

Referring to FIG. 8B, in one embodiment, surface feature 810 may include a single bulbous surface feature 812 (e.g., a ring or loop) that protrudes radially from and extends around a full circumference of a presently described medical device.

Figure 8C:
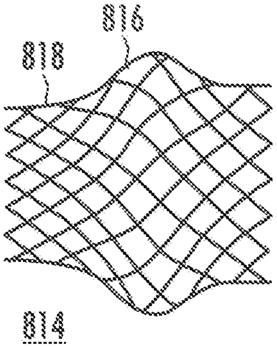

Referring to FIG. 8C, in another embodiment, surface feature 814 may include a single bulbous surface feature 816 that protrudes radially from and extends around a full circumference of a ramped portion 818 of a presently described medical device, wherein ramped portion 818 comprises a smaller diameter on one side of bulbous surface feature 816 than on the other.

Figure 8D:
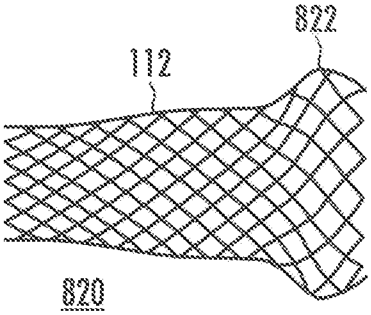

Referring to FIG. 8D, in another embodiment, surface feature 820 may include a single bulbous surface feature 822 that protrudes radially from and extends around a full circumference of flare 112, as described with respect to FIG. 1A.

Figure 8E:
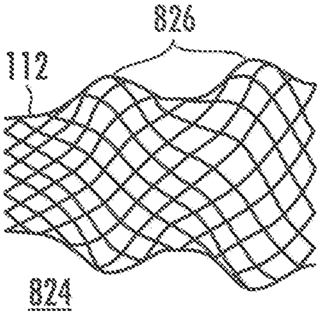

Referring to FIG. 8E, in another embodiment, surface feature 824 may include a pair of spaced-apart bulbous surface features 826 that protrude radially from and extends around a full circumference of flare 112.

Figure 8F:
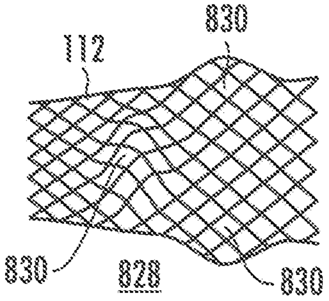

Referring to FIG. 8F, in another embodiment, surface feature 828 may include a series of radially-oriented spaced-apart bumps or projections 830 disposed in a symmetric or asymmetric pattern around a full circumference of flare 112.

Figure 8G:
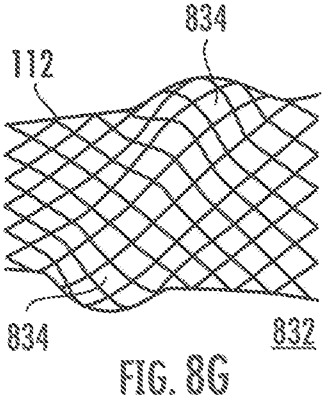

Referring to FIG. 8G, in another embodiment, surface feature 832 may include a single bulbous surface feature 834 that protrude radially from and extends in a spiral or helical configuration around a full circumference of flare 112.

Figure 8H:
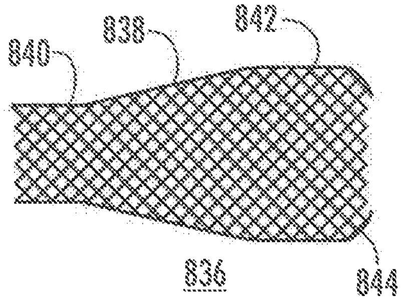

Referring to FIG. 8H, in another embodiment, surface feature 836 may include an extended ramp 838, for example, that extends between a first portion 840 and a second portion 842, where the second portion has a diameter that is greater than a diameter of the first portion 840, for example, twice as great. The ramp 838 may include a length as great as a diameter of retention member 216, as great as a diameter of lumen 204, twice as great as a diameter of lumen 204, or other length. Second portion 842 may be a cylindrical portion having a length one half the length of ramp 838, the same length as 840, or other length. The second portion 842 may have an inwardly curving end 844 (e.g., curling end) may provide an atraumatic tissue interface.

Figure 8I:
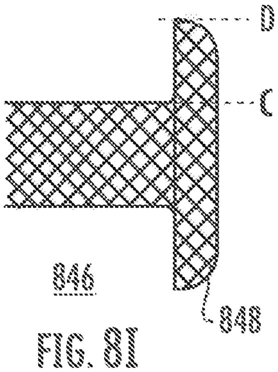

Referring to FIG. 8I, in another embodiment, surface feature 846 may include an inverted end 848, which curls back so that tangential lines ("C" and "D") drawn from the beginning and end of the inverted end 848 form an interior angle greater than 90 degrees, thereby providing an atraumatic tissue interface and/or a grasping curl at the end of a presently described medical device. As illustrated, for example, tangential lines C and D form an interior angle of 180 degrees.

It will be understood that surface features as described herein may be used singly in a medical device, or they may be used in any combination desired such that multiple surface features are provided in a single medical device. It will also be understood that any or all of the surface features may comprise a variety of inflection points, curves, straight lines, etc., and may be paired or otherwise combined in any combination to reduce migration risk of a medical device as presently disclosed.

Although the medical devices 100, 214, 300, 320, 330, 700 disclosed herein are generally depicted as including woven, knitted or braided filaments (e.g., Nitinol, etc.), in various embodiments, the medical devices may include laser cut designs which may or may not change in length (e.g., shorten) as the medical device moves from the first configuration to the second configuration. The medical devices in various configurations may be self-expanding or expandable such as balloon-expandable.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

The invention claimed is:

1. A medical device, comprising:

an elongate tubular body comprising first and second end portions, the elongate body having a constrained configuration and an unconstrained configuration;

wherein the first end portion of the elongate tubular body is doubled back towards the second end into a retention member such that the first end portion overlaps the elongate tubular body a length greater than a length of the retention member;

the elongate tubular body comprising a coating or covering of the retention member and extends beyond the first end portion towards the second end portion along a partial axial length of the medical device;

wherein an uncovered segment of the first end portion extends beyond the retention member towards the second end portion.

2. The medical device of claim 1, wherein the uncovered segment extends beyond the retention member radially outward of the covering or coating.

3. The medical device of claim 1, wherein the second end portion is uncovered.

4. The medical device of claim 1, wherein the retention member is fully covered.

5. The medical device of claim 1, wherein the retention member comprises at least one flange.

6. The medical device of claim 1, wherein the coating or covering extends towards the second end portion along at least 50% of a full axial length of the medical device.

7. The medical device of claim 1, wherein the elongate tubular body in the unconstrained configuration is configured to facilitate fluid flow without leakage between the second end portion and the retention member.

8. The medical device of claim 1, further comprising a second retention member in the unconstrained configuration, the second retention member including a flare, step, bulb, raised braid segment, or any combination thereof.

9. The medical device of claim 1, further comprising at least one radiopaque, echogenic, or colored marker.

10. The medical device of claim 1, wherein the medical device is a self-expanding stent.

11. A medical device, comprising:

an elongate body having a constrained configuration and an unconstrained configuration, the elongate body including:

a first end and a second end;

a retention member at the first end, the retention member having a doubled back configuration such that the first end overlaps the elongate body a length greater than a length of the retention member;

a first portion extending from the retention member towards the second end, the first portion having a covering extending towards the second end from the retention member at least partially along an axial length of the first portion; and a second portion extending towards the second end from the retention member along a radially outer surface of the first portion, the second portion having a shorter axial length than the first portion, and wherein the second portion is uncovered.

12. The medical device of claim 11, wherein the retention member comprises a covering.

13. The medical device of claim 11, wherein the retention member comprises at least one flange.

14. The medical device of claim 11, wherein the covering extends towards the second end along at least 50% of the axial length of the medical device.

15. The medical device of claim 11, further comprising a second retention member in the unconstrained configuration, the second retention member including a flare, step, bulb, raised braid segment, or any combination thereof.

16. The medical device of claim 11, further comprising at least one radiopaque, echogenic, or colored marker.

* * * * *